(12) United States Patent
Logue

(10) Patent No.: US 7,692,632 B2
(45) Date of Patent: Apr. 6, 2010

(54) FOOT-OPERATED COMPUTER INPUT DEVICE

(75) Inventor: Rebecca L. Logue, Meridian, ID (US)

(73) Assignee: Beckmer Products, Inc., Meridian, ID (US)

( * ) Notice: Subject to any disclaimer, the term of this patent is extended or adjusted under 35 U.S.C. 154(b) by 0 days.

(21) Appl. No.: 12/495,773

(22) Filed: Jun. 30, 2009

(65) Prior Publication Data

US 2010/0001948 A1  Jan. 7, 2010

Related U.S. Application Data

(63) Continuation-in-part of application No. 12/116,182, filed on May 6, 2008, now Pat. No. 7,554,526, and a continuation-in-part of application No. 10/973,999, filed on Oct. 25, 2004, now Pat. No. 7,369,116.

(60) Provisional application No. 60/513,929, filed on Oct. 23, 2003.

(51) Int. Cl.
*G06F 3/033* (2006.01)
*G09G 5/08* (2006.01)

(52) U.S. Cl. ........................ 345/163; 345/156

(58) Field of Classification Search .......... 345/156–168
See application file for complete search history.

(56) References Cited

U.S. PATENT DOCUMENTS

| | | | | |
|---|---|---|---|---|
| 5,712,460 A * | 1/1998 | Carr et al. | ................... | 200/86.5 |
| 6,179,829 B1 * | 1/2001 | Bisch et al. | .................... | 606/1 |
| 6,611,250 B1 * | 8/2003 | Prince et al. | ................. | 345/163 |
| 6,812,918 B2 * | 11/2004 | Yang | ........................... | 345/167 |
| 6,866,507 B2 * | 3/2005 | Beerstecher | ................ | 433/101 |
| 6,975,303 B2 * | 12/2005 | Dalsey | ........................ | 345/163 |
| 2008/0129683 A1 * | 6/2008 | Li | .............................. | 345/156 |

\* cited by examiner

*Primary Examiner*—Ricardo L Osorio
(74) *Attorney, Agent, or Firm*—Pedersen & Co., PLLC; Ken J. Pedersen; Barbara S. Pedersen

(57) ABSTRACT

A foot operated data entry/input pad has a plurality of foot-operated buttons. The foot buttons may be used to enter data values, such as numbers or symbols separately or in combination. Each button is preferably capable of entering different data values, preferably depending on the length of time that it is pressed or on the number of times that it is pressed in succession. A small controller may be included to allow the user to control the computer's pointer, allowing the user to switch between data entry fields. A heel rest may serve as both a heel rest and a button/switch for sending an electric/electronic signal. An automated voice system, or other audible and/or visual indicator system, may help the user keep track of the data value as it changes and is entered. In alternative versions for input of instructions, single values or binary information, or for selection of items in a pull-down screen window, a pad may have two buttons provided adjacent a cursor controller, wherein the cursor controller and right and left click buttons are on an arc or on an angle.

11 Claims, 28 Drawing Sheets

FOOT-OPERATED COMPUTER INPUT DEVICE

This application is a continuation-in-part, and claims priority, of U.S. Non-Provisional Ser. No. 12/116,182, filed May 6, 2008, issuing as U.S. Pat. No. 7,554,526, on Jun. 30, 2009, entitled "Foot-Operated Key Pad", which is a continuation-in-part, and claims priority, of U.S. Non-Provisional application Ser. No. 10/973,999, filed Oct. 25, 2004, issued on May 6, 2008 as U.S. Pat. No. 7,369,116, which claims priority of Provisional Application Ser. No. 60/513,929, filed Oct. 23, 2003, and entitled "Foot-Operated Data Entry Pad," the entire disclosures of said applications and patents being incorporated herein by this reference.

BACKGROUND OF THE INVENTION

1. Field of the Invention

This invention relates to data entry and/or other input devices for computers, and more particularly to foot-operated data entry/input pads.

2. Related Art

As an example of data entry, measuring and recording the depth of a periodontal pocket caused by a periodontal disease, such as gingivitis, is one of the most important diagnostic activities in dental care. There are many known apparatus for taking these measurements. Commonly, these measurements are entered into a digital database via a computer. However, conventionally, the dental worker taking the measurements has been unable to enter the data manually without having to put down the measuring instruments and move his/her hands to a computer keyboard and/or mouse to record the measurements. Thus, the job is often performed by two or more workers, wherein one worker takes the measurements and the other worker enters them into the computer. Thus, there is a need for such a data entry system that can be operated easily without the use of hands.

For example, Grenfell, et al. (U.S. Pat. No. 3,943,914) attach a foot pedal to an automatic probe used to measure gingival sulcus. The user positions the probe for measurement, and then activates the foot pedal. This triggers the automatic probe to take a depth measurement and transmit the result to the data recording system. Other devices, such as Murphy, et al. (U.S. Pat. No. 4,904,184); Murphy (U.S. Pat. No. 5,144,753); Jeffcoat (U.S. Pat. No. 5,318,442); and Matoba, et al. (U.S. Pat. No. 5,993,209) have similarly used a footpad to instruct an instrument to take a measurement and transmit the reading to a data recording system.

Ackerman, et al. (U.S. Pat. No. 5,197,487) use a foot activated switch to switch between different modes of operation for analyzing and organizing data from a probe. However, the switch is not used to actually enter any data.

Eenboom, et al. (U.S. Pat. No. 4,446,453) disclose a foot pad capable of very simple data entry. This device is capable of entering a bare yes/no response for the presence of plaque on a patient's teeth. Matoba, et al. (U.S. Pat. No. 5,993,209) also teach a device that also is used to indicate whether plaque is present on a patient's teeth.

None of these devices are capable of entering information beyond a simple binary data set—e.g., yes or no, either/or, or on or off.

Also, there are references which disclose foot-operated controls for computers. For example, Hayes, et al. (U.S. Pat. No. 5,552,807) discloses foot pedal controls for both flying and driving games. Also, Bookstein (U.S. Pat. No. 5,838,305) and Howell (U.S. Pat. No. 6,091,402) disclose foot-operated control of the position and movement of the computer's cursor. Also, Klarlund (U.S. Pat. No. 5,889,510) disclose a foot-operated keyboard with two arrays of switches—one in the toe-resting region, and one in the heel-resting region. Also Cochran, et al. (U.S. Pat. No. 5,910,139) and Davidson, et al. (U.S. Pat. No. 6,470,222) disclose remote control of surgical and/or dental instruments with a foot pedal controller. However, there is still a need for a foot-operated data entry system capable of allowing entry of a wider range of data, such as numeric or alphanumeric information.

There is also a need for foot-operated data entry/input devices for uses in fields other than dentistry, for example, other medical settings, various businesses and offices, warehouses and manufacturing facilities, and governmental, welfare, or charitable agencies. There is especially a need for a foot-operated data entry/input device in many fields wherein the user must, or prefers to, keep his/her hand(s) available for operation or handling of other equipment, material, or paper. Medical uses may include, but are not necessarily limited to, patient-intake, X-ray, ultrasound, and other imaging, and emergency room data management. These medical settings, as well as the other business and industrial settings, for example, may benefit from a foot-operated device that is simple relative to the preferred embodiments of the dental care versions of the invention. Thus, there is still a need for a foot-operated data entry/input device that is comfortably and easily operated by the user's foot and that may be used in addition to, or in place of, a conventional, hand-operated computer "mouse."

SUMMARY OF THE INVENTION

The invention is a foot-operated data entry and/or other input pad for cooperation with a computer and/or computerized equipment. The foot-operated pad may be adapted for entering informational data over a desired range for recordation, for maneuvering around a computer screen, and/or for inputting selections or instructions such as those typically done with a "right click" and a "left click" of a hand-held computer mouse. In preferred embodiments, one or more foot buttons are provided and a joystick or other cursor controller is provided, with said foot buttons and joystick/controller preferably being arranged in an arc-shaped pattern on the pad so that the user's foot may comfortably and consistently pivot generally horizontally between the buttons and joystick/controller, preferably with minimal or no movement of the heel of the user's foot, with certainty and accuracy.

In embodiments preferably adapted for the dental field, data corresponding to numbers is entered by pressing the appropriate foot button. Foot buttons are arranged in a spaced-apart, generally radial planar pattern, distanced about ⅔ of an average foot length (about 5-10 inches) from a heel rest region. Optionally, the heel rest region may also comprise another switch. Preferably, different discreet values may be entered by pressing the same foot button different lengths of time or, in an alternative embodiment, by repeatedly pressing it. Additionally, in the embodiments preferably adapted for the dental field, a joystick-type or other controller is used to control the computer's pointer, as it is often necessary to move a cursor between data entry fields.

Preferably, the data entry/input pads, whether adapted for the dental field or for other medical, business, or industrial fields, will work seamlessly with existing hardware and software by mimicking at least portions of a mouse and/or keyboard—i.e., the computer receives and processes input from the data entry/input pad as signals from a mouse and/or keyboard.

Optionally, the data entry/input pad may include an automated voice system that announces entered values and/or the current value to be entered if the user releases a foot button or otherwise ceases to cause the data value to increment.

In preferred embodiments for medical fields other than dentistry, or for business or industry in general, the data entry/input pad comprises an arc-shaped or a radial planar pattern of at least one button on each of two sides of a joystick/cursor controller, wherein the joystick/controller is preferably a pad that may be rocked by the foot in any direction (forward, rearward, to each side and in any combination of these directions to result in 360 degree movement) to move a cursor as needed. The at least one button on each side of the joystick/controller preferably includes buttons adapted for right and left click functions. Preferably, the pad is adapted to be switchable to right-footed use or left-footed use, so that the electronics for the buttons to the right and left of the joystick/cursor controller may be switched prior to use to make either button the right click or the left click button. These embodiments may be equipped with an extension/portion of the pad on which the user may rest his/her heel. Alternatively, these embodiments may not be sized and shaped for such an extension/portion, in which case the user rests or holds his/her heel off of and behind the pad, preferably on the floor behind the pad.

Alternatively, the controller and data entry functions may be separated into two separate devices, or the controller function may be omitted. Multiple data entry/input pads may also be used together to increase the capacity of the system.

DETAILED DESCRIPTION OF THE PREFERRED EMBODIMENTS

Referring to the Figures, there are shown several, but not all, embodiments of the invented foot operated data entry/input pad. Data entry/input pads according to various embodiments of the invention may integrate with a larger system that preferably includes a computer, with its usual accessories—i.e., mouse, keyboard, and monitor (not shown)—and preferably an adapter, called a multiplexer, that allows the footpad to interface seamlessly with existing computer hardware and software. The preferred multiplexer connects to the data entry pad and the computer's other input devices—i.e., mouse and keyboard—and controls their respective signals so that the computer perceives all input as though it came only from the mouse or keyboard. Thus, with the preferred embodiment, there is no need for additional or new software and the data entry pad can be integrated easily with existing systems.

The term "data" is used herein to refer to information to be stored for later retrieval. In the preferred embodiment, the data is an integer referring to the depth of a periodontal pocket, measured in millimeters. However, the term "data" may include any information represented by numbers or other symbols, such as letters, that is stored for later review. The term "data" as used herein does not refer to instructions, such as sent by a controller for a pointer or program operation, such as a video game control. "Data" also does not refer for this invention to simple binary data sets—i.e., where one of two options, such as yes or no, red or green, or on and off is the only correct choice. The terms "instruction" or "instructions" refer to single pieces of information to be input, single options such as entering "yes" as a selection of an item after a cursor has been moved to a particular location on the computer screen or a pulled-down "window" of the computer screen, and binary data sets such as yes or no, red or green or on and off, for example.

Figure 1:
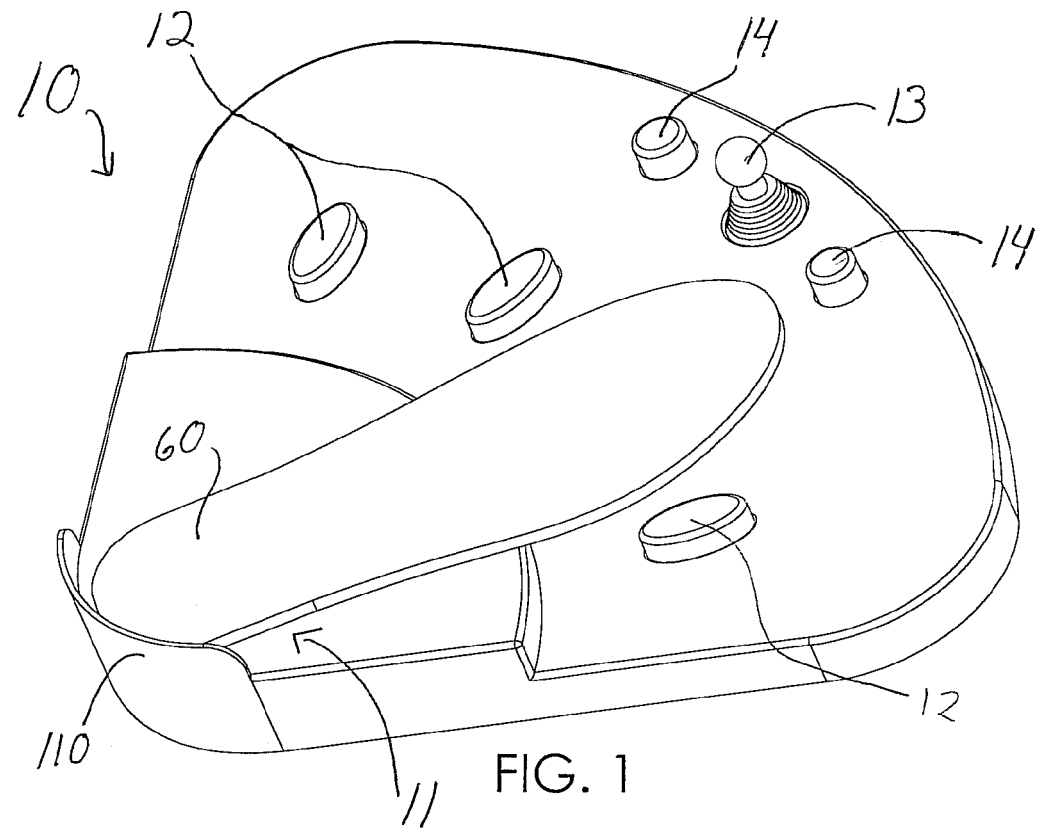
FIG. 1 is a perspective view of one embodiment of the invented foot-operated data entry pad with a schematic shoe sole included for illustrative purposes. When the term "foot" is used herein, this means that the foot may be covered or partially covered by a shoe, other footwear, or a sock/stocking, and/or that the user in some instances may even use the device with a bare foot.
Figure 2:
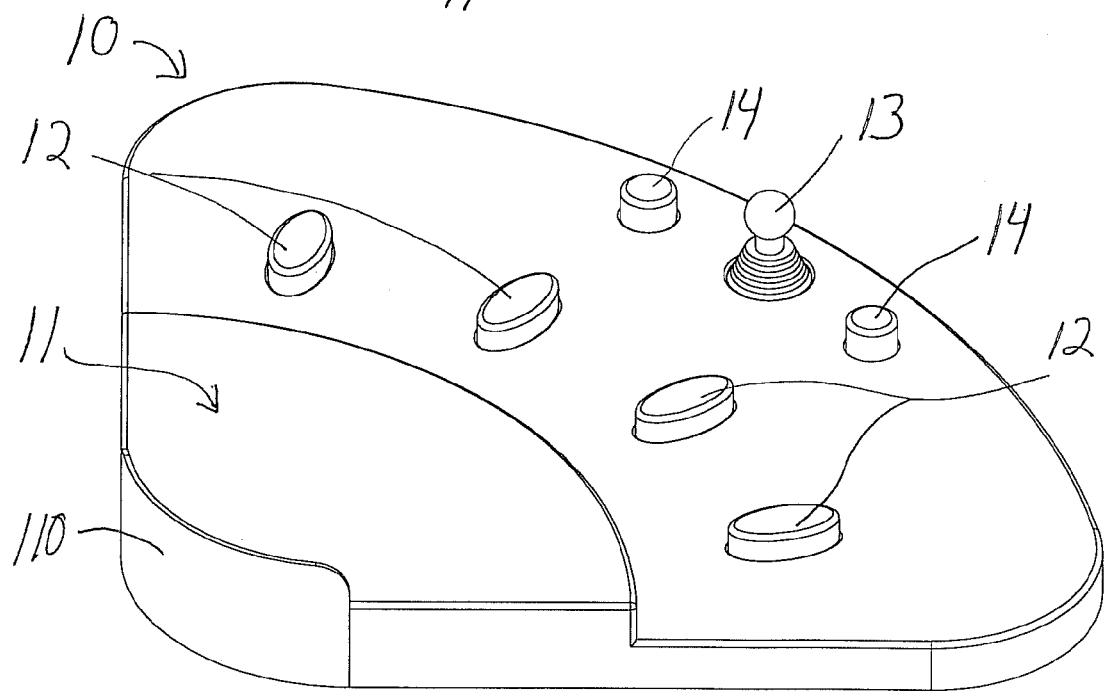
FIG. 2 is a perspective view from a slightly different angle of the embodiment of FIG. 1 with the schematic shoe sole removed.

Referring to FIGS. 1 and 2, one embodiment of the invented data entry pad 10 comprises a heel support area 11 with heel support rear wall 110, plurality of foot buttons 12, controller 13, and one or more controller buttons 14. The user places the heel of the foot on heel support 11 and pivots the foot on that point to reach each of the foot 12 buttons. The foot buttons 12 are arranged in a spaced-apart, generally radial planar pattern. This way, the data entry pad operator may access each of the buttons singly, without disturbing the other buttons. Also, this way the operator may access each of the buttons by simply rotating the foot about the heel which is in the heel support area 11. By pivoting the foot on its heel, the distal portion of the foot moves in a generally radial planar pattern, to reach each of the foot buttons as desired, wherein each foot button may be considered to be in its respective circle sector, the center of which circle is preferably at or near the heel support area 11. The top surfaces of the foot buttons, and/are preferably on the same or generally the same plane (hence, a "planar pattern") but do not necessarily have to be exactly on the same plane. The top surface of the joystick/cursor controller may be on a different plane than the top surfaces of the buttons (see FIGS. 1-4 and 7, 13 24), or may be on the same, or generally the same, plane (see FIGS. 27-36).

Typically, the foot buttons 12 are spaced-apart about 1½-5½ inches. Also typically, the foot buttons are distanced about ⅔ of an average foot length (about 5-10 inches) from the center of heel support area 11. The foot button radial pattern may extend in an expanding pie shape out from the heel support area 11 from about 30° to abut 150°, depending upon the number of buttons in the pattern. The buttons may be present in one or more rows. When there are multiple rows of buttons, preferably they are staggered to maximize distance between the buttons.

As described in more detail below, the data value sent to the computer preferably depends on which foot button 12 is pressed and also on the number of times, or the length of time, that it is pressed. As illustrated by the inclusion of foot sole 60 in FIG. 1, controller 13 and controller buttons 14 are preferably beyond the reach of the user's foot when the heel is touching heel support rear wall 110 to prevent accidental activation of controller 13 and/or controller buttons 14. Other foot buttons 12 could be added to the data entry pad to mimic, for example, the shift key, control key, or mouse buttons, etc. Alternatively, controller button 14 may be replaced by designing heel support area 11 to register and transmit a signal—e.g., either mouse button signal—when heel support area 11 is pressed down by the user's heel. In some applications, one or both of controller buttons 14 could be omitted.

The preferred foot buttons 12 are Hall-effect sensors. They are preferably narrower than a foot to allow them to be closer together and position-error tolerant. If foot buttons 12 were as wide as a foot, the user would have to move his foot at least one foot-width between foot buttons 12, and foot buttons 12 would have to be spaced at least one foot-width apart (take up at least one foot-width on the data entry pad). If foot buttons 12 are, as in the preferred embodiment, only one-half inch in diameter, then when the user is pressing one foot button 12, the other foot buttons 12 can be close to the user's foot on either side. Therefore, the preferred space between foot buttons 12 is one-half foot-width plus one-quarter inch, about 3 inches. As a result, the user only has to rotate the foot by this reduced pitch, for example, from one small circle sector to an adjacent small circle sector. This gives more foot buttons 12 for the same ankle rotation, or reduces the amount of ankle rotation for a given number of buttons. Alternatively, heel support area 11 could be designed to allow the user's heel to move laterally, by sliding or lifting it, to reach foot buttons 12 while reducing or eliminating the need for ankle rotation.

Each foot pedal key can be used for multiple purposes by double-clicking or by holding down for an extended time. For example, the "one button" may indicate the data value "one" if held down for less than one second. If the "one" button is held for one second or longer, for example, it becomes a "five". Voice feedback can say "one" if the pedal is released before one second, and it can say "five" at the one second point so that the user knows to release the button. In the case of two functions per button, the data can be transmitted either at the transition time or upon pedal release. Additional functions can be achieved by holding the button longer still. Also, mouse functions and keyboard functions can be mixed. For example, holding the "four" button for less than one second corresponds to the data value "four," and holding the "four" button one second makes it an "eight" button (corresponding to the data value "eight" rather than "four"), but holding it for three seconds makes it a mouse "right click" button. If there are three or more functions per pedal, the data cannot be transmitted until the pedal is released. If there are three or more functions, the voice feedback can simply announce the next functional level or can insert a substitute word such as "rather" before the function or data name (e.g., "rather, nine").

Figure 8:
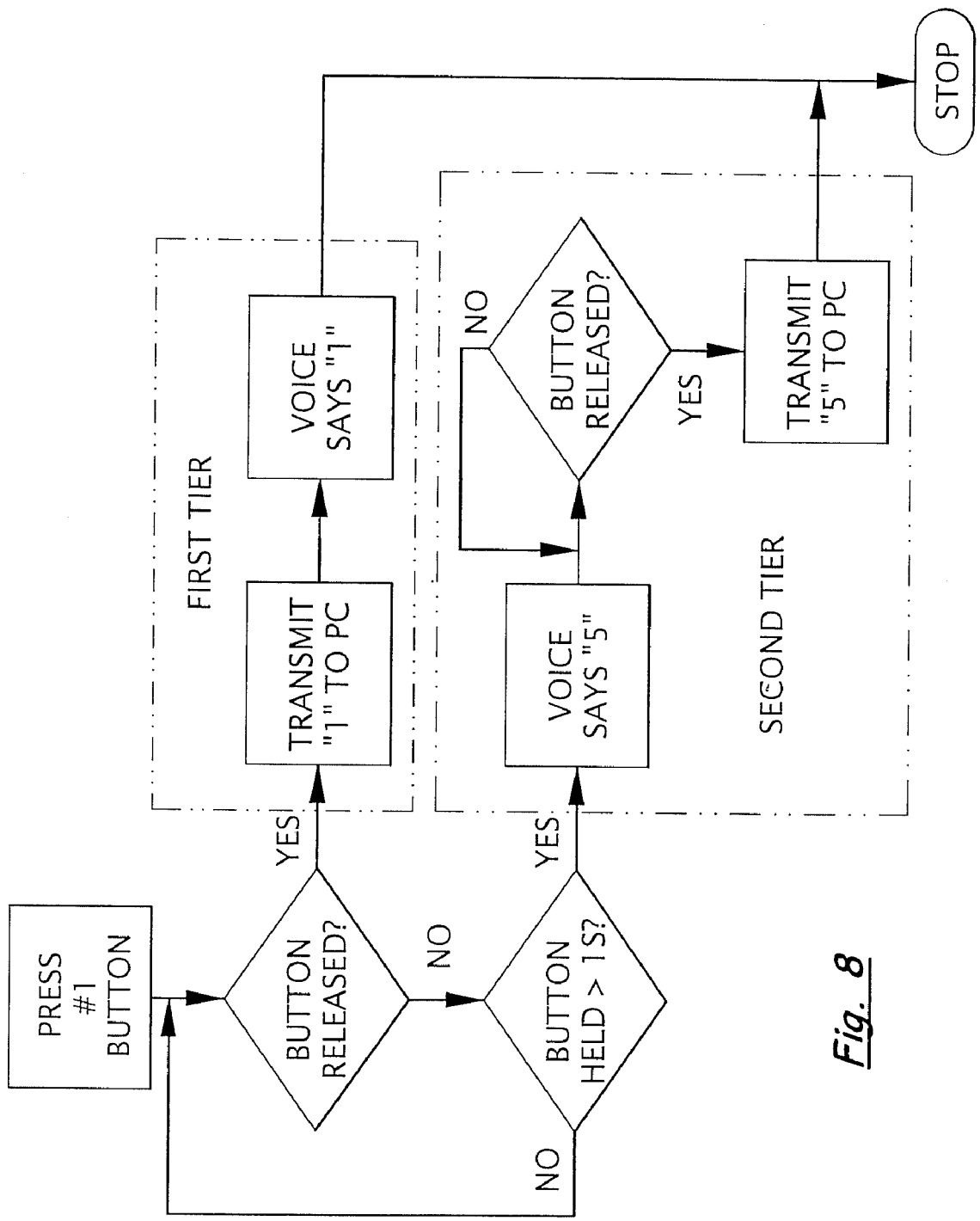
FIG. 8 is a logic flow diagram illustrating the foot button operation of the preferred embodiment of the invention, for example, that may be adapted for use in dentistry, for example.

Referring to FIG. 8, the operation of the foot buttons in the preferred embodiment for dental application is illustrated. The first foot button 12, with an initial data value of 1, is used for illustrative purposes. Preferably, each foot button 12 is capable of entering more than one data value. This is preferably accomplished by making the data value entered dependent on which foot button 12 is pressed and on how often or on how long it is continuously pressed.

To enter a given data value, the user presses the appropriate foot button 12, but the data value is preferably sent to computer 51 only after foot button 12 is released. For example, if the chosen foot button 12 is released before a set time period—preferably one second—has passed, the initial data value associated with the chosen foot button 12 is transmitted to an automatic voice system, which announces the data value, and to the computer system for recording. As illustrated in FIG. 8, the resulting data value would be 1. The other three foot buttons 12 have initial data values of 2, 3, and 4. If the foot button is not released in less than the set period of time—i.e., one second for the preferred embodiment—the initial data value is increased by four, and the new value is sent to the automated voice system for announcement, but not to the computer system. The data value is sent to the computer system once the foot button is released. Optionally, the data value could be reannounced as entered at this point.

In the preferred embodiment, each foot button 12 is associated with two data values—e.g., 1 and 5 for the first button, as illustrated in FIG. 8—covering the integers from one to eight, inclusive. Although the preferred embodiment permits entry of only a small range of data values, any appropriate data values can be chosen as the upper and lower limits, including no upper limit or infinity—or an upper limit, and no lower limit with descending rather than ascending numbers. Thus, continuing to hold foot button 12, in this example, could result in the data value increasing by four—i.e., to 9, 13, etc.—infinitely or, preferably, to any appropriate maximum for a given application. Also, the increment between data values need not be one, or any other value, but can be set at any appropriate amount for a given application. Besides,

[1] This routine is for each button. Any number of buttons can be used.

[2] Digit entry is shown here, but entry can be any digit, character, symbol, word, phrase, etc., that is desired to be entered into the PC.

[3] Wait times between increments can be set to any value to optimize usability.

[4] More tiers of increments can be added. The voice says something new after each increment time period, but the entry is not transmitted until the button is released.

Figure 9:
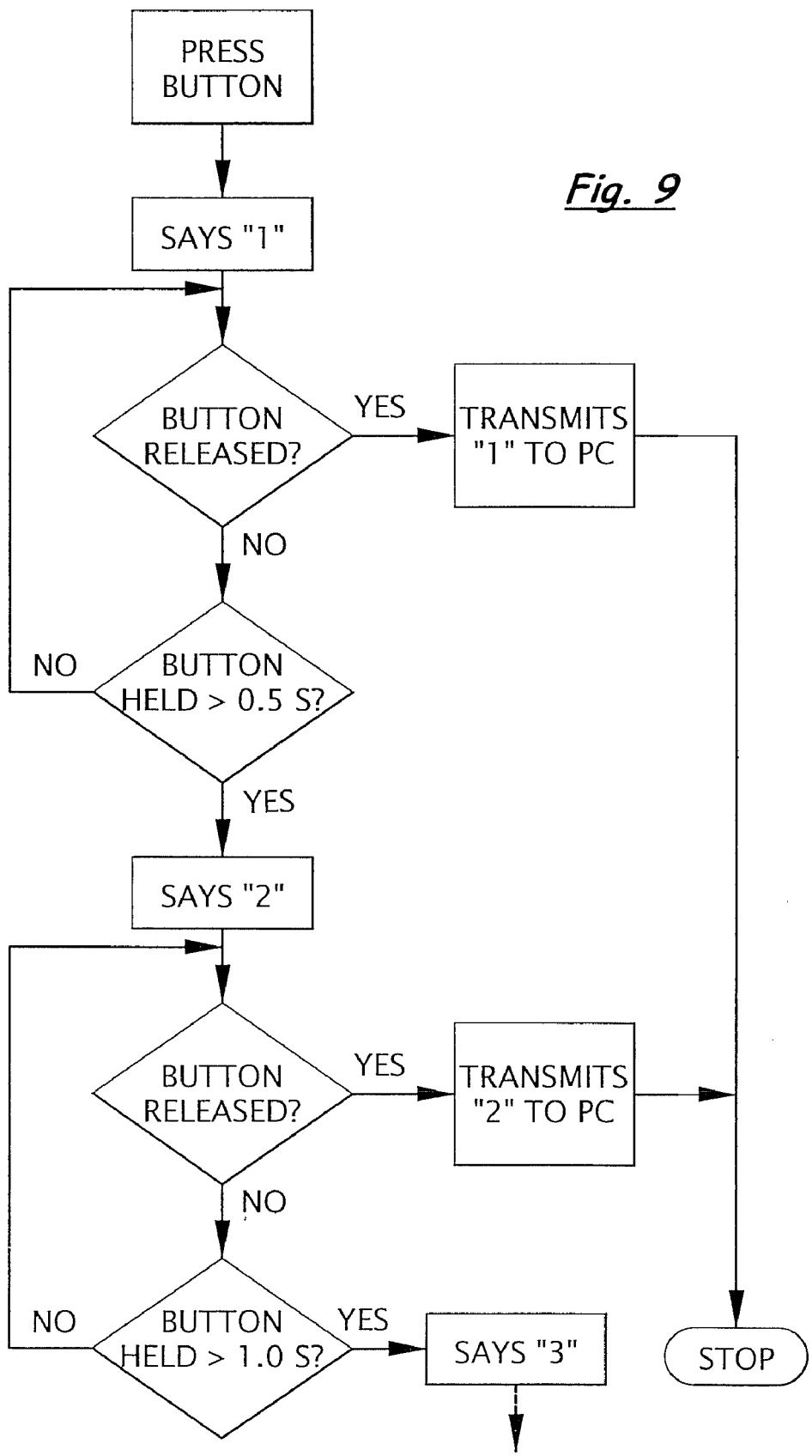
FIG. 9 is a logic flow diagram illustrating the foot button operation of an alternative embodiment of the invention, which may be adapted for use in dentistry, for example.

Referring to FIG. 9, the operation of the foot buttons in one alternative embodiment is illustrated. In this example, the initial data value is 1 and increases by increments of 1. This could be the case where there is only one foot button 12, where the initial data values for other foot buttons 12 are non-integers—e.g., 1.25, 1.5, and 1.75—or where other foot buttons 12 operate for number ranges wholly greater or lesser than those for the foot button 12 in the example—e.g., one button could be used to enter values from 1 to 10, another to enter values from 11 to 20, and so on. In the embodiment of FIG. 9, the button is held down until the desired entry is heard. Then, upon releasing the button, the entry is transmitted to the PC. The set time period after which the data value is increased is 0.5 seconds rather than the 1.0 second of the preferred embodiment—any time period can be chosen, but it should preferably be long enough for the user to release the foot button 12 before the data value changes without being so long as to make the device unproductively slow. No limit to the values that can be entered is shown in the embodiment of FIG. 9, but one could be added. Likewise, any increment between data values may be chosen, depending on the needs of any given application. When the chosen foot button 12 is pressed, the initial data value is sent to the automated voice system and announced. Each time the data value changes, it is sent to the automated voice system and announced. The data value is sent to the computer only after the chosen foot button 12 is released. Optionally, this data value could be re-sent to the automated voice system and reannounced as entered.

Figure 10:
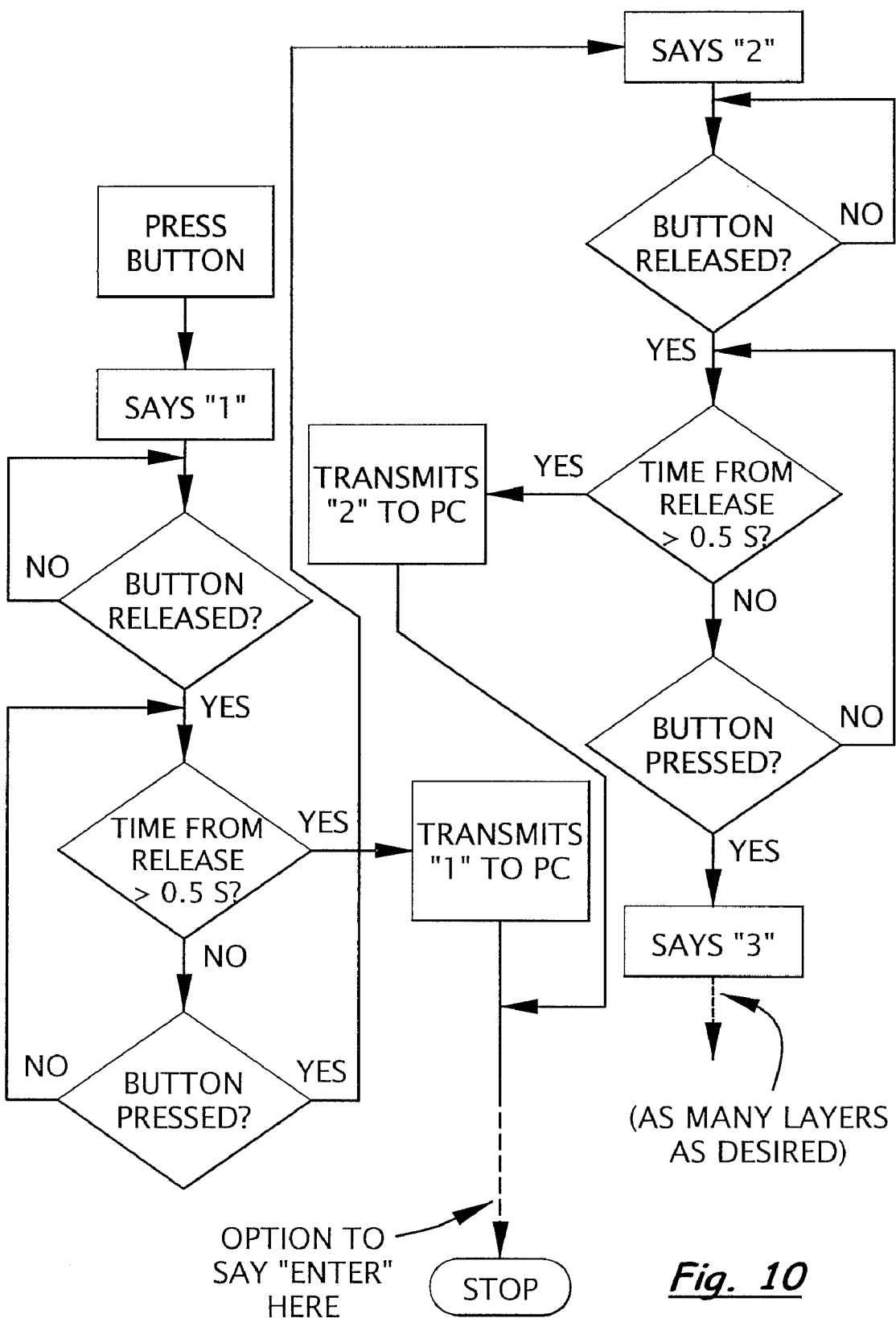
FIG. 10 is a logic flow diagram illustrating the foot button operation of another alternative embodiment of the invention, which may be adapted for use in dentistry, for example.

Referring to FIG. 10, the operation of the foot buttons in another alternative embodiment is illustrated. In this variation, the button is pressed and released until the desired entry is heard. Then, when the button has been released for over ½ second, the entry is transmitted to the PC. In this case, a chosen foot button 12 is pressed, released, and re-pressed within a set period of time to enter a data value. Like the embodiment of FIG. 9, the initial data value is "one" and the increment between data values for a foot button 12 is 1. When the appropriate foot button 12 is pressed, the associated initial data value is announced. When the button is released, the device waits a preset period of time—in this case, 0.5 seconds—to see whether the button is re-pressed. If the button is not re-pressed, the data value is sent to the computer system. If the button is re-pressed during the preset time period, the data value is incremented and the new value announced. This process is repeated with increasing data values until the button is not re-pressed within the preset time period. At that point, the last data value is sent to the computer system. As with the other embodiments, limits on the range or data values enterable may be imposed for convenience, but are not required. Likewise, the increment between data values may be set at any amount appropriate for a given application.

The techniques discussed above relating to FIGS. 8-10 with timing or repeat features amount to a code of actuation for the foot buttons(s). For example, as will be understood from the above discussion, the code of actuation may depend upon how long a button is continuously depressed, or, the code of actuation may depend upon how many times a button is depressed, released, and re-depressed.

Most people are not able to accomplish fine motor movements with their feet. Therefore, it is a further aspect of the preferred embodiments of the invention to develop a joystick which can precisely position a cursor on a computer screen, but which doesn't require accurate foot movements. The joystick is digital, meaning that it is on or off rather than proportional. If it is pressed up, the cursor begins moving up. If it is released, the cursor stops. The joystick does not control cursor position or cursor speed. It only controls approximate direction of travel. In the preferred embodiment, the joystick will only move in eight discrete directions (up, right, 45 degrees up and right, etc.). Alternatively, the joystick could be made to move the cursor in any direction. The cursor can move at a constant speed, but in the preferred embodiment, it starts out slowly and then increases its speed more as the joystick is pressed longer. In this way, quick on-and-off, in a form of "dithering", motions can achieve very fine cursor manipulation, while pressing the joystick longer can cause the cursor to traverse the screen in a reasonable amount of time. Although applicable to foot operation, this feature of the preferred embodiments of the invention can also be used for a hand-operated device for those who cannot perform fine-motor movements with their hands.

In the preferred embodiment, the user is able to perform any point-and-click operations that the user's software includes with controller 13 and one or more controller buttons 14. The preferred controller 13 is a short joystick. Alternatively, a rocking panel may be used. Controller 13 controls the cursor by causing it to move in a chosen direction. Optionally, the speed of the cursor may be adjustable and/or increasing the longer controller 13 is held off-center. Preferably, one or more controller buttons 14 are placed to one or both sides of controller 13. Alternatively, a controller button 14 may placed in the center of the controller 13 so that when the controller is released, the button is released and activated to send a computer mouse left or right button signal to computer 51. Because controller 13 and controller buttons 14 are placed beyond the reach of the user's foot when the foot is contacting heel support rear wall 110, the user moves his foot forward from heel support rear wall 110 to operate controller 13 and controller buttons 14. In the preferred embodiment, controller buttons 14 mimic the functions of the left and/or right mouse buttons.

Digits or other data can be input using one of several foot pedals or buttons. For example, the heel or foot can rest on a pivoting platform, pad, cradle, or footrest. When the pivoting member rotates about an axis roughly parallel with the ankle, its rotational position may be sensed by optical, mechanical, Hall-effect, proximity, or other means and is interpreted as being in one of N positions. For example, four discrete positions can be detected using only two discrete detectors. If the detectors are optical, then an interrupter, cam, or reflector plate could trigger only the first detector, both detectors, only the second detector, or no detectors. Depending upon which of these four combinations is detected, the correct data is selected for transmission. Then the data can be entered, for example, by rocking the pivoting foot device about a second axis roughly perpendicular to the first. When the foot device rocks, it detects the rotational motion. Alternatively, the foot could rock forward (whether the foot device pivots or is shaped to allow the foot to rock) and touch a button or bar or be sensed in another way to activate a switch, and initiate an entry.

Figure 3:
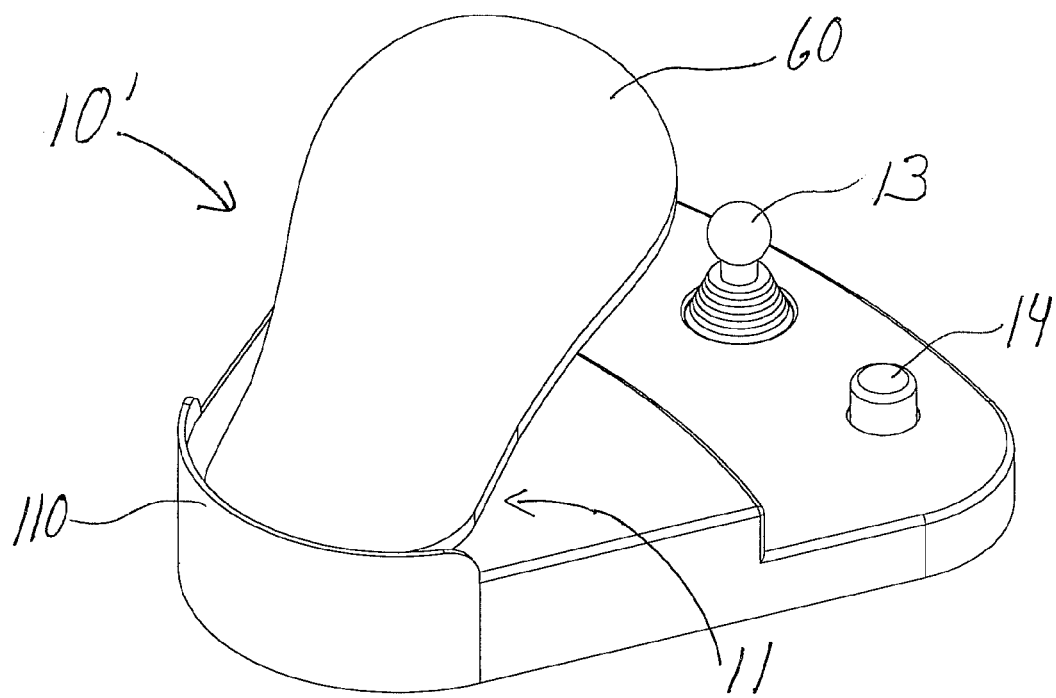
FIG. 3 is a perspective view of one alternative embodiment of the invented data entry pad with a schematic shoe sole included for illustrative purposes.
Figure 4:
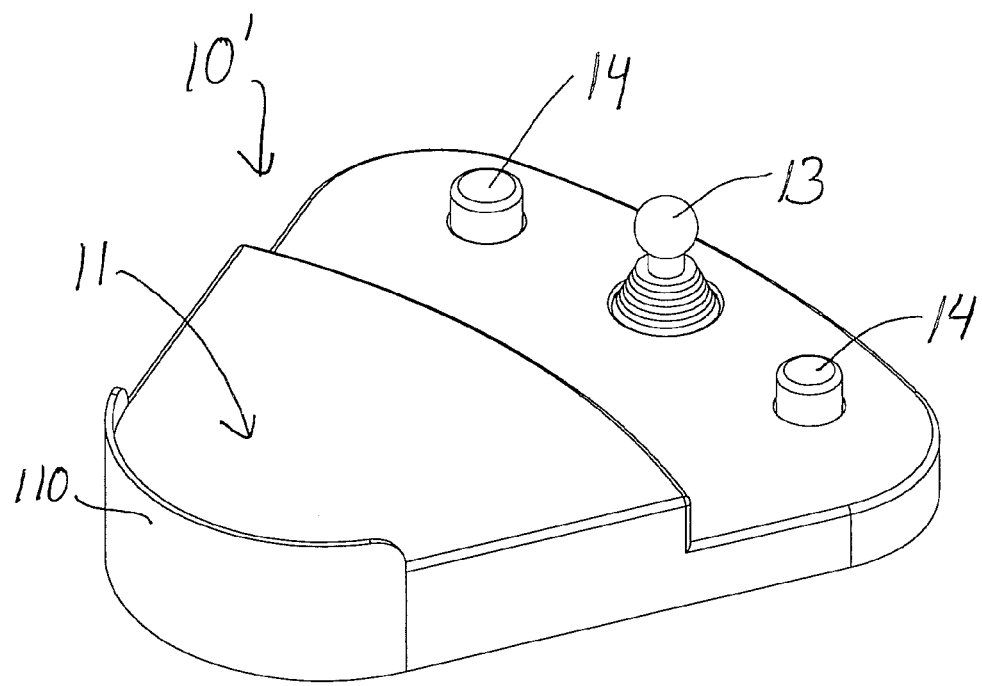
FIG. 4 is a perspective view of the embodiment of FIG. 3 with the schematic shoe sole removed.
Figure 5:
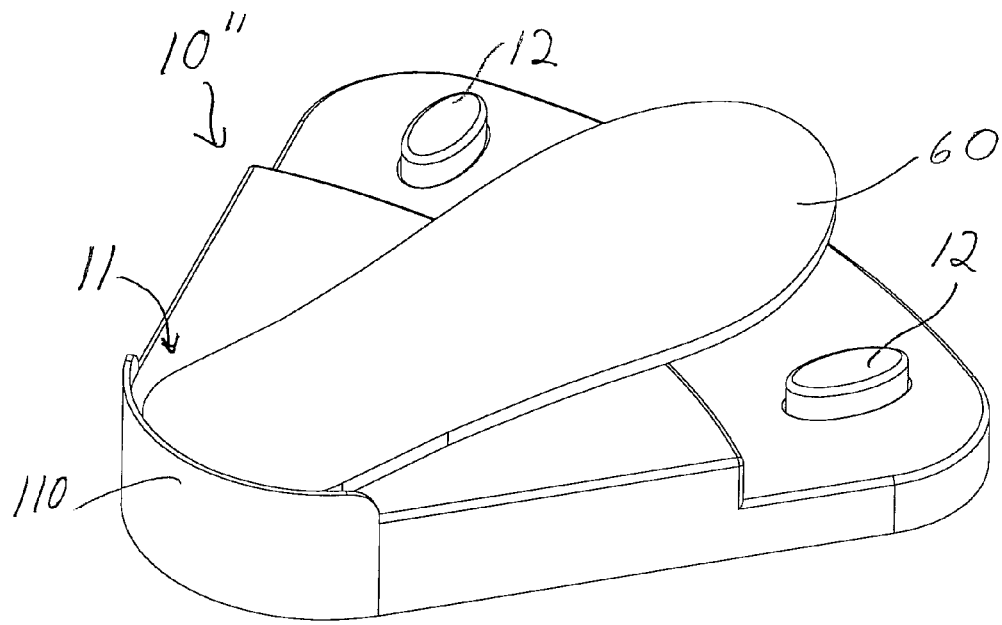
FIG. 5 is a perspective view of another alternative embodiment of the invented data entry pad with a schematic shoe sole included for illustrative purposes.
Figure 6:
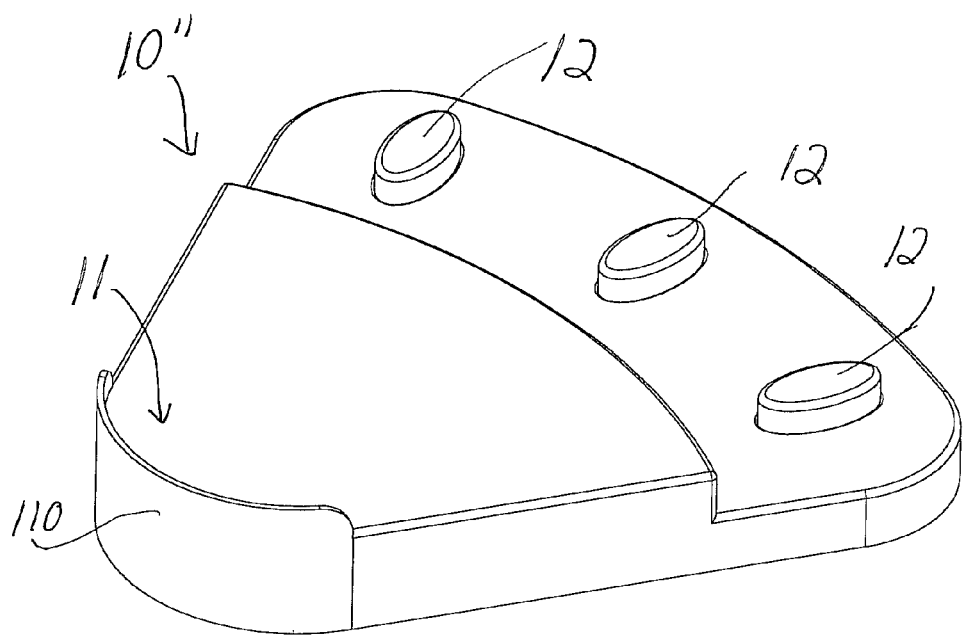
FIG. 6 is a perspective view of the embodiment of FIG. 5 with the schematic shoe sole removed.

Referring to FIGS. 3 and 4, one alternative embodiment is data entry pad 10' with only controller 13 and controller buttons 14 is shown. Controller 13 and controller buttons 14 function as in the preferred embodiment, described above, except that the user can operate controller 13 and controller buttons 14 without moving his feet forward from heel support 11, as illustrated by foot sole 60 in FIG. 3, because the overall length of the data entry pad 10' is shorter than the preferred embodiment, pad 10. In this embodiment, there are no foot buttons 12. Controller 13 and controller buttons 14 may be actuated with a simple heel rotation before applying pressure on controller 13 and buttons 14 with the toes or ball of the foot. Moving on to FIGS. 5 and 6, an alternative embodiment of data entry pad 10" is shown. It is shown with three foot buttons 12, and with no controller or controller buttons. Foot buttons 12 function as in the preferred embodiment, described above, except that the interval between data value points is three rather than four because of the number of foot buttons 12 included. For example, the "one" button (for example, the button 12 at the far left in FIGS. 5 and 6) may correspond to the data value "one" when held for less than one second (or less than a first time mark), but may correspond to the data value "four" when held for one second or more (or equal to or more than said first time mark). Likewise, the "two" button (in the middle, preferably) may correspond to the data value "two" when held for less than one second (or less than a first time mark), but may correspond to the data value "five" when held for one second or more (or equal to or more than said first time mark). The "three" button (at the right, preferably) may correspond to the data value "three" when held for less than one second (or less than a first time mark), but may correspond to the data value "six" when held for one second or more (or equal to or more than said first time mark). Data entry pad 10" may be designed to use other data values and different time marks, however; for example, said code of actuation may comprises a first data value being transmitted to the computer when the foot button is continuously pressed for a time equal to or less than one second and released, and a second data value being transmitted to the computer when the foot button is continuously pressed for more than one second and then released.

Preferably, the two embodiments in FIGS. 3-6, data entry pad 10' and data entry pad 10" are used in conjunction, giving the user all the capabilities of the preferred embodiment, data entry pad 10 of FIGS. 1 and 2. The user may operate each device with a separate foot or may switch his foot back and forth, as the user prefers.

Figure 7:
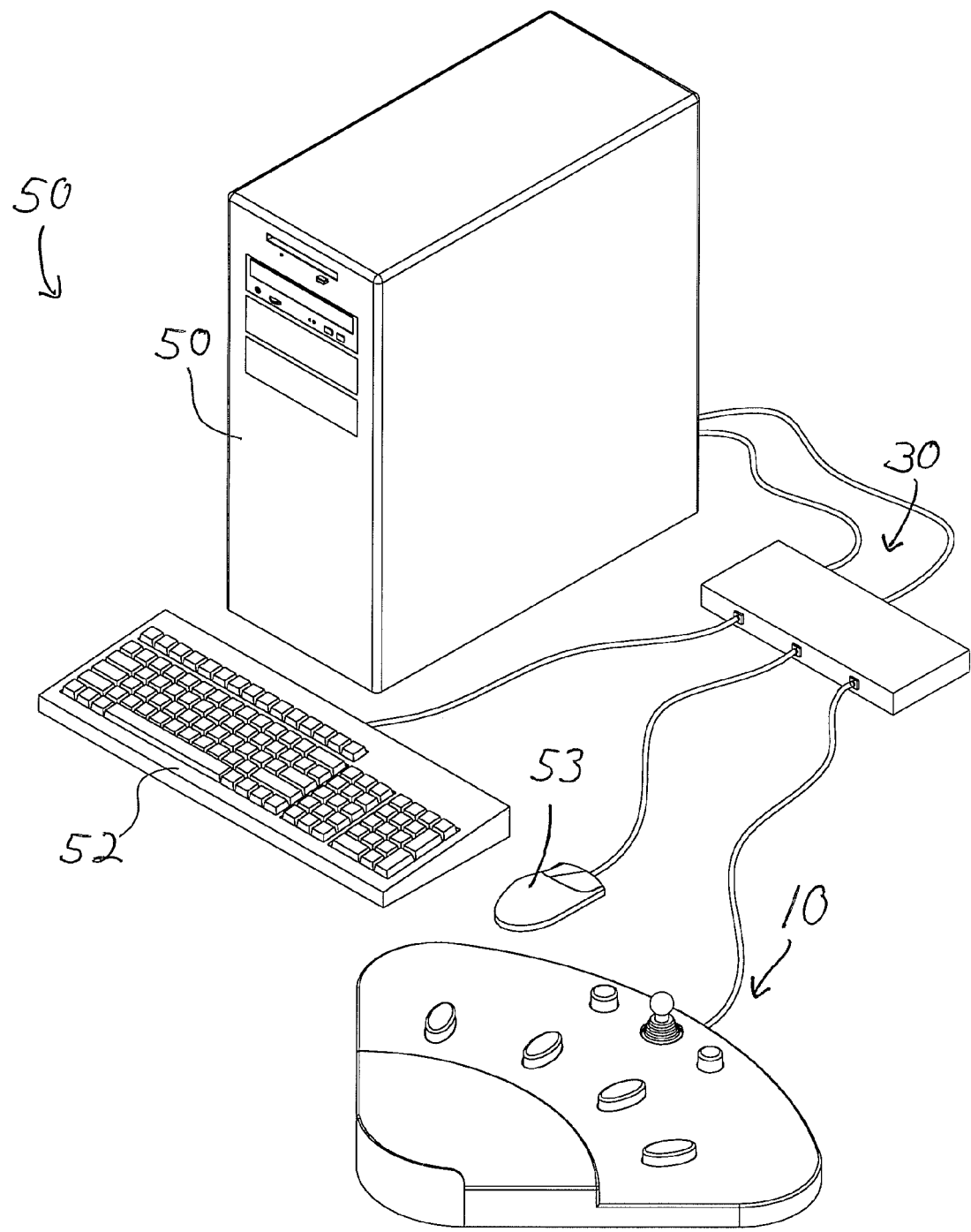
FIG. 7 is a perspective view of the embodiment of FIGS. 1 and 2 in connection with one embodiment of a computer system.

Referring to FIG. 7, the preferred embodiment of data entry pad 10 is illustrated connected to a typical computer system 50 used for data entry. Data entry pad 10 is connected to multiplexer 30. Mouse 53 and keyboard 52 are also connected to multiplexer 30. Multiplexer 30 is connected to computer tower 51 via two cords, which connect to the computer's mouse and keyboard ports (not shown). Multiplexer 30 receives signals from keyboard 52, mouse 53, and data entry pad 10. Signals from data entry pad 10 are identified as mouse-type or keyboard-type signals. Signals from all input devices are prioritized and sent to the appropriate computer port—i.e., the mouse or keyboard port. Although the preferred embodiment is shown connected to computer system 50 via wires, any or all of the connections may be wireless using any wireless technology—e.g., methods used for a wireless mouse or wireless laptop connections.

Ideally, the data input device should be connected to the computer in a way that is invisible to the application software. Connecting to the serial port would require modifying application software to look for data input at that port. Connecting to a USB port is simple, but in some cases will require installing special driver software. This is a reasonable approach, as it will be invisible to the application software that is manipulating or storing the data. The preferred embodiment is to input data and cursor movement through the mouse and keyboard PS/2 ports. This is where the computer and application software receive their data and cursor instructions.

Unplugging the keyboard and mouse to connect the foot pedal/pad, then changing back for hand-typing additional data would be unacceptable, especially because the computer must be turned off to plug and unplug devices to the PS/2 ports. Therefore, a means to mix or multiplex the signals from mouse and joystick and mix the signals from the keyboard and foot pedal/pad is required.

Figure 11:
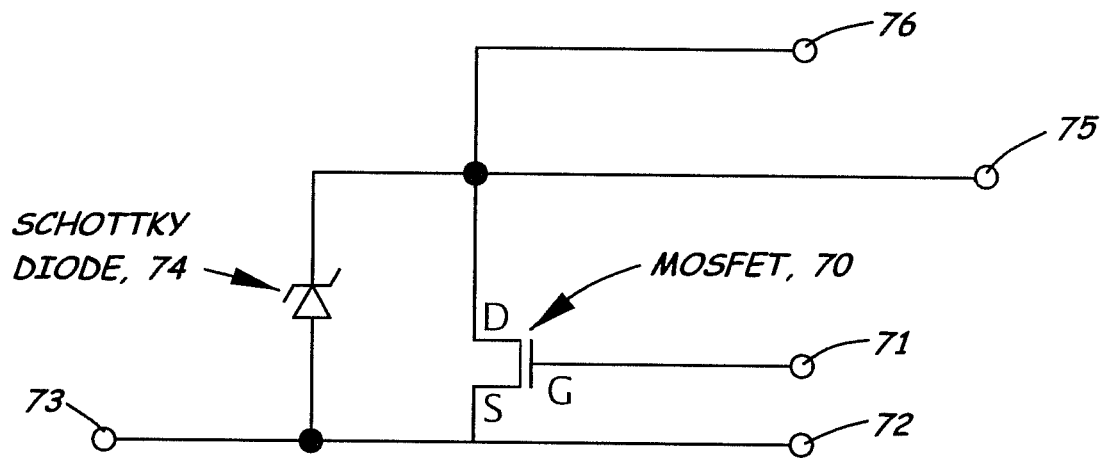
FIG. 11 is a schematic wiring diagram of the clock line circuit for the multiplexer of the preferred embodiment of the invention.
Figure 12:
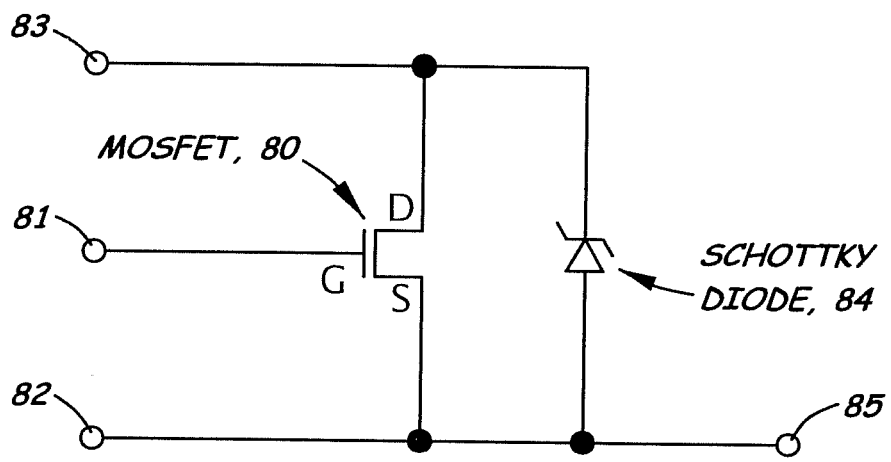
FIG. 12 is a schematic wiring diagram of the data line circuit for the multiplexer of the preferred embodiment of the invention.

There are several ways to accomplish this multiplexing or "wye" connection.

a) An 8-pole, double throw switch could connect the four mouse lines and four keyboard lines from the computer to either the keyboard and mouse, or to the foot pedal/pad and joystick device.

b) All the ground/common/negative lines could be permanently connected together and a 6-pole, double throw switch can be used to connect the remaining lines.

c) Adding a large capacitor between power and ground lines on the computer side of these switches could minimize the effects of hot switching.

d) The ground/common/negative lines could be permanently connected together, the power lines could be permanently connected together, and then a 4-pole, double throw switch would connect the two data lines and two clock lines. This requires that power consumption of the foot pedal/pad device plus keyboard and mouse to be low enough to fit within the PS/2 specification for computer-supplied power.

e) Same as (d) above, but power is augmented with a wall transformer. For example, if optical detectors are used, their LEDs could be powered by an auxiliary power source.

f) The switches in the scenarios above could be replaced by solid-state switching devices or relays.

g) The scenarios above all require the user to flip a switch to change between devices. A smart technique would allow input to be received from any device without user intervention. The user should be allowed to seamlessly switch from keyboard to foot pedal/pad and mouse to joystick, and vice-versa. One way to accomplish this is to use one or two micro-controllers to manage the communication between the peripheral devices and the PC. In PS/2 communication, the PC is the host. If the micro-controller acted like a host to the keyboard and mouse it could receive their input data and could also receive data from the foot pedal/pad. Then the micro-controller could act like a slave to the PC, looking like a keyboard and mouse. In this way it could input the data from all devices while looking like one keyboard and one mouse. Communication between the foot pedal/pad and micro-controller could be PS/2, I²C, or any other proprietary or standard protocol, or the foot pedal/pad sensors could input directly to the micro-controller. The micro-controller could pass signals in near real time, mimicking the clock and data signals from a peripheral or PC, or it could process one data byte or packet at a time before relaying it to the PC. While the micro-controller is sending data from the foot pedal/pad to the PC, it can pull the keyboard clock line low to inhibit the keyboard. The keyboard will buffer any data it has to send until the clock line goes high. In this way, data from the keyboard, mouse and foot pedal/pad can be inter-mixed (multiplexed) to be fed to the PC in the order it is input by users, and at a speed still exceeding the user's ability to enter the data. Data from all devices gets processed and the computer cannot tell whether a cursor movement was initiated by a mouse or joystick, or whether data is coming from a keyboard or foot pedal/pad.

h) A micro-controller between a keyboard and PC or between a mouse and PC will cause signal delays which could potentially result in malfunction. Therefore, the preferred embodiment uses N-type, logic level MOSFETs and Schottky diodes to connect and disconnect the signals between these devices. See the FIGS. 11 and 12 following. FIG. 11 illustrates a Clock Line Circuit: MOSFET 70, to micro-controller output (to switch keyboard connection) 71, to open collector output of micro-controller (to inhibit keyboard) 72, to keyboard clock line 73, Schottky diode 74, to PC clock line 75, to open collector output of micro-controller (to drive clock line) 76. FIG. 12 illustrates a Data Line Circuit: MOSFET 80, to micro-controller output (to switch keyboard connection) 81, to open collector output of micro-controller (to drive data line) 82, to keyboard data line 83, Schottky diode 84, to PC data line 85. The clock line circuit (FIG. 11) and data line circuit (FIG. 12) of a PS/2 port are open collector; they float high with the help of a resistor and can be pulled low by either the PC or peripheral device (keyboard or mouse). When the devices are connected (MOSFETs are turned on by pulling gates high), the keyboard or mouse can communicate directly with the PC and there is essentially no signal delay. The device pulls the clock line low through the MOSFET and pulls the data line low through the diode. The PC pulls the device clock line low through the diode and pulls the data line low through the MOSFET. When the MOSFETs are turned off (gates are pulled low), the device is disconnected, the device is inhibited by pulling its clock line low, and the clock and data lines on the PC side can be manipulated by the micro-controller to communicate foot pedal information to the PC. In this disconnected state, the device clock line is already low, so clock transitions on the PC side will not be changing the clock line through the diode, but the diode allows the line to go high. When the device is inhibited, it will let its data line float high. The data line on the PC line can go high and low while being isolated from the device by the diode.

i) A further aspect of preferred embodiments of the invention is that the micro-controller can monitor communication between a device and the PC. One use of this is to determine which kind of mouse to emulate. The PC queries the mouse at start-up to determine which kind of mouse it is, and therefore knows how to read and interpret the mouse information it receives. If the micro-controller monitors this communication, it can then emulate that same kind of mouse in its communication. This allows the multiplexer to be universal in application with any standard PS/2 mouse.

j) Although less user friendly, a simpler implementation to select between the most common mouse types is to use configuration switches set at the factory or by the user. For example, one setting would cause three-byte mouse packets to be transmitted and another setting would cause four-byte mouse packets to be transmitted.

k) Watching PC-to-mouse communication also allows the micro-controller to capture and emulate the same resolution, scaling, and other factors relevant to cursor movement.

m) The keyboard or mouse can be kept in an inhibited state for several milliseconds after the micro-controller transmits a foot pedal/pad command to see if the PC sends a "resend" command. If so, the micro-controller must retransmit its last data.

n) If the voltage drop across the Schottky diode is problematic, then an open-collector op-amp/comparator circuit can be used as a buffer to follow signals to their low-level state. A rail-to-rail op-amp will achieve an almost perfect zero voltage.

o) Many N-type MOSFETs have a diode between their source and drain. If their voltage drop is not a problem, then it is possible to implement the circuit without the external diode shown in the sketch.

Although the preferred embodiment of the invention is shown at one size, various methods may be used to accommodate various sizes of feet and/or to accommodate "left-footed" people rather than "right-footed" people or to fit a particular required placement/space on the floor. For example, models may be made in different sizes. More preferably, heel support area 11 and/or heel support rear wall 110 may be made adjustable so that it may be moved forward or backward—i.e., along a line passing through the center of heel support 11 and controller 13. The adjustment method may be continuous—i.e., may be set at any point—or have discreet setting—i.e., a plurality of locking points. Additionally or instead, heel support rear wall 110 may be eliminated in order to allow some rearward adjustability for heel placement; preferably, however, the data entry pad is adapted for use with the heel and foot on the pad rather than off of the pad (rather than on the floor, for example).

Figure 13:
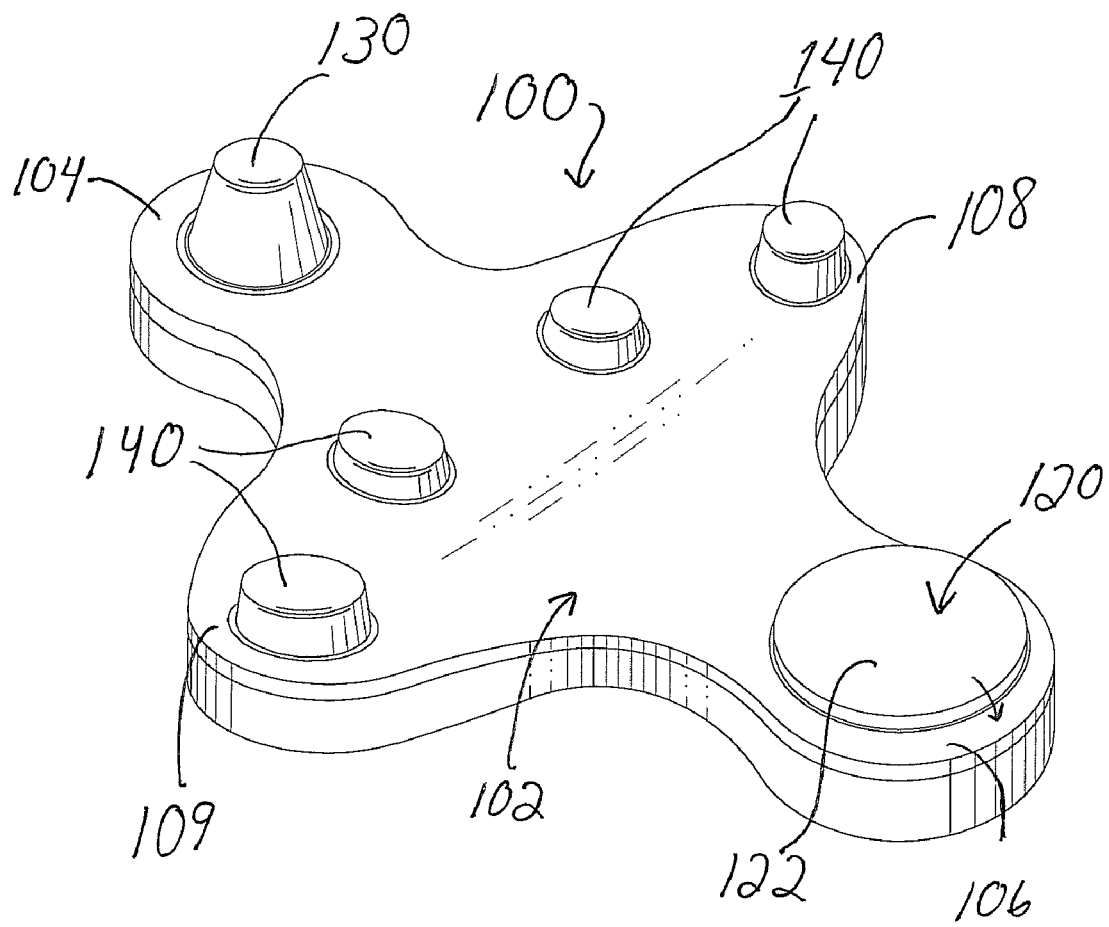
FIG. 13 is a perspective top, left-side view of another embodiment of the invented foot-operated data entry pad, which may be adapted for use in dentistry, for example.
Figure 14:
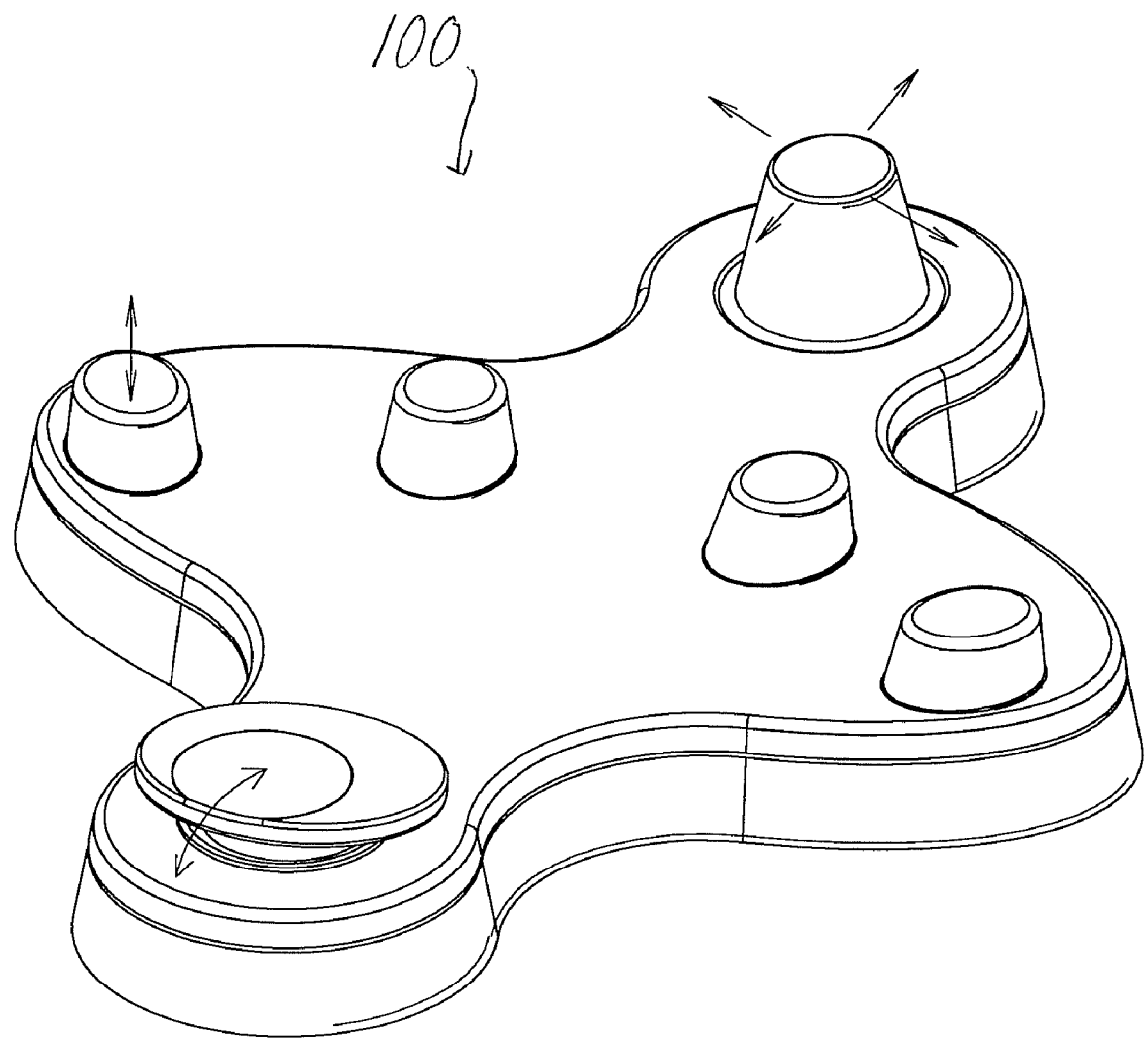
FIG. 14 is a top, right perspective view of the embodiment of FIG. 13.
Figure 15:
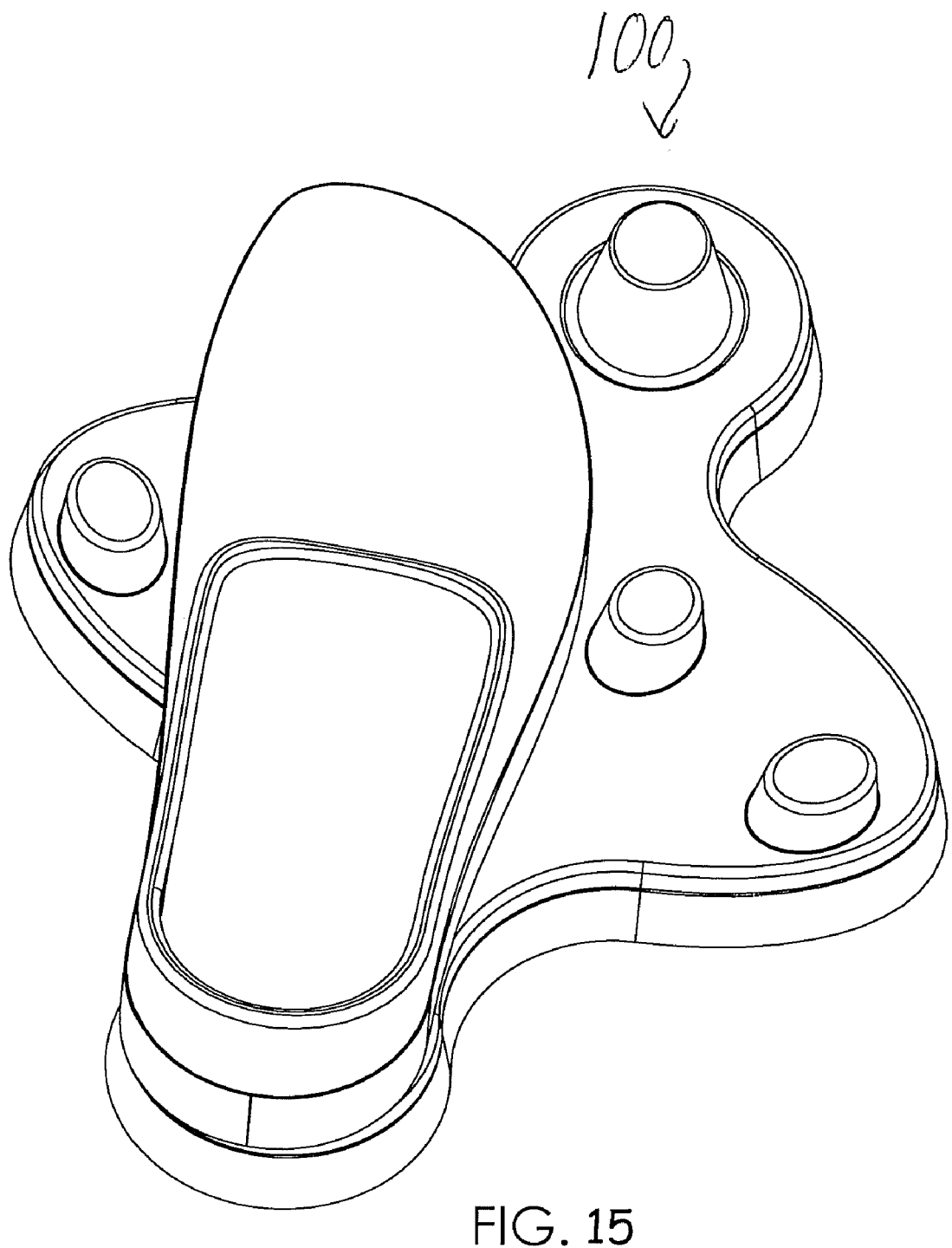
FIG. 15 is a rear perspective view of the embodiment of FIGS. 13 and 14, with a shoe on the pad illustrating use of the pad.
Figure 16:
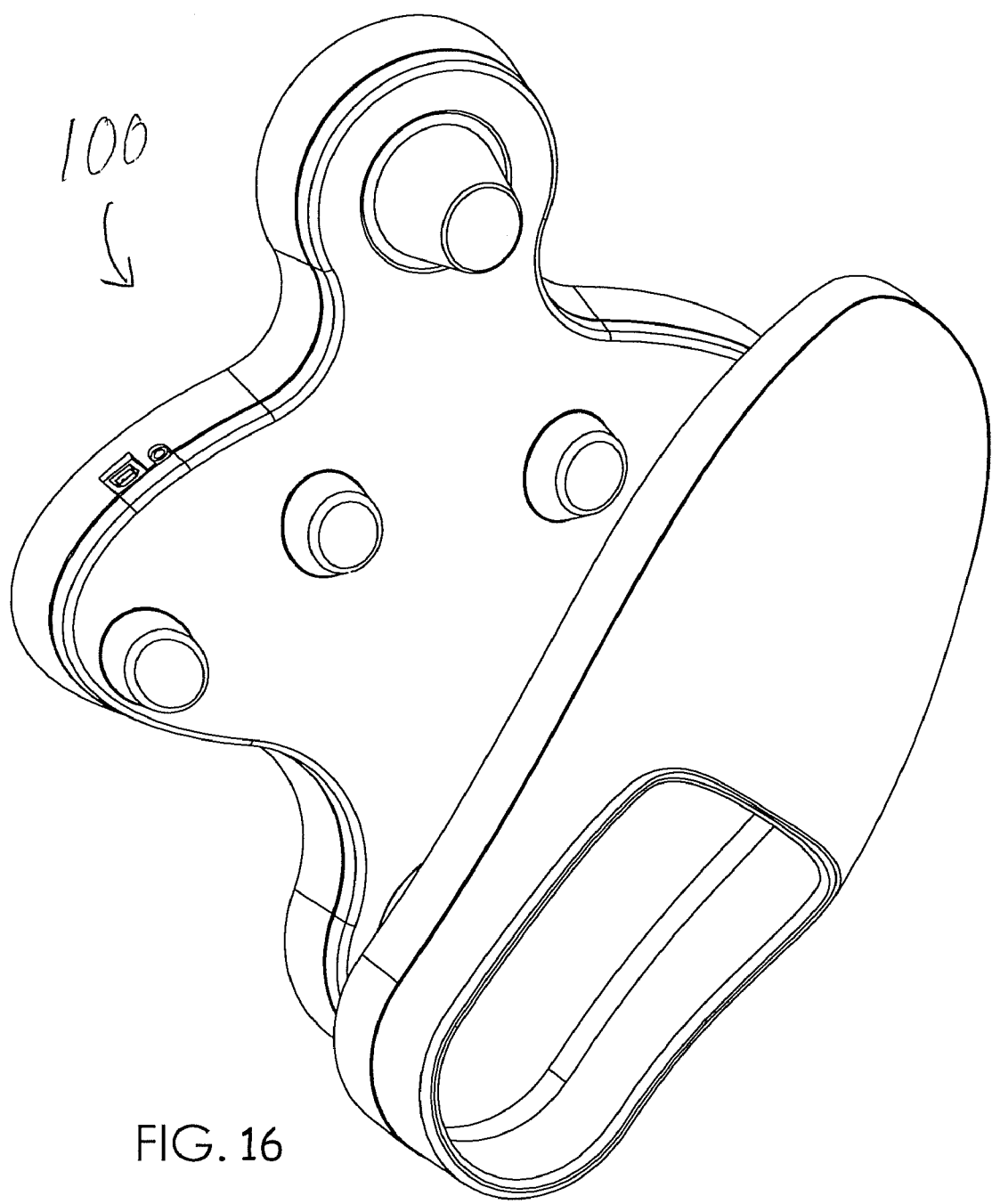
FIG. 16 is a front-left perspective view of the embodiment of FIGS. 13-15, with a shoe on the pad illustrating use of the pad by pressing the far-right button.
Figure 17:
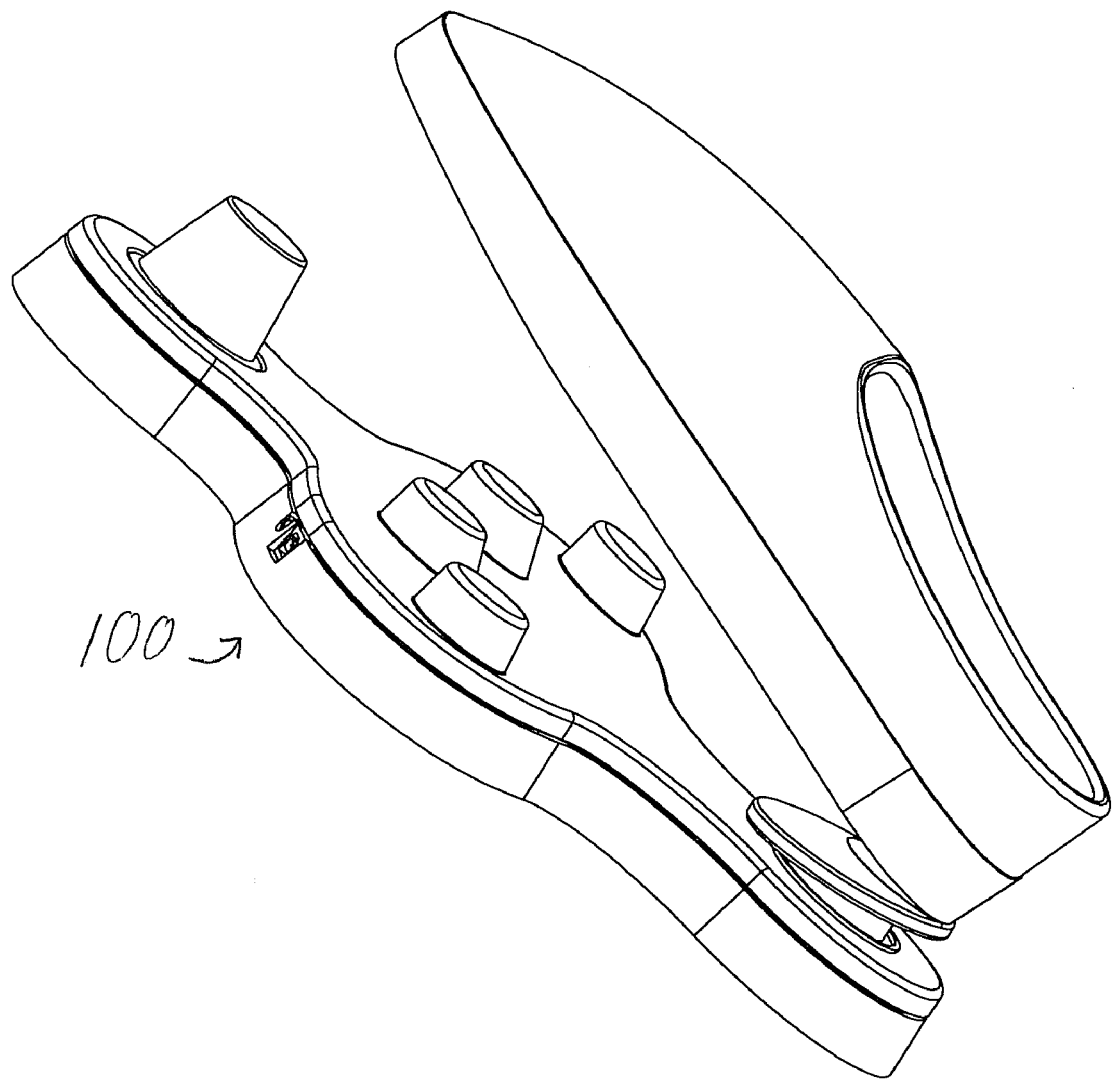
FIG. 17 is a left-side perspective view of the embodiment of FIGS. 13-16, illustrating the user rocking rearward on the heal support of the pad.
Figure 18:
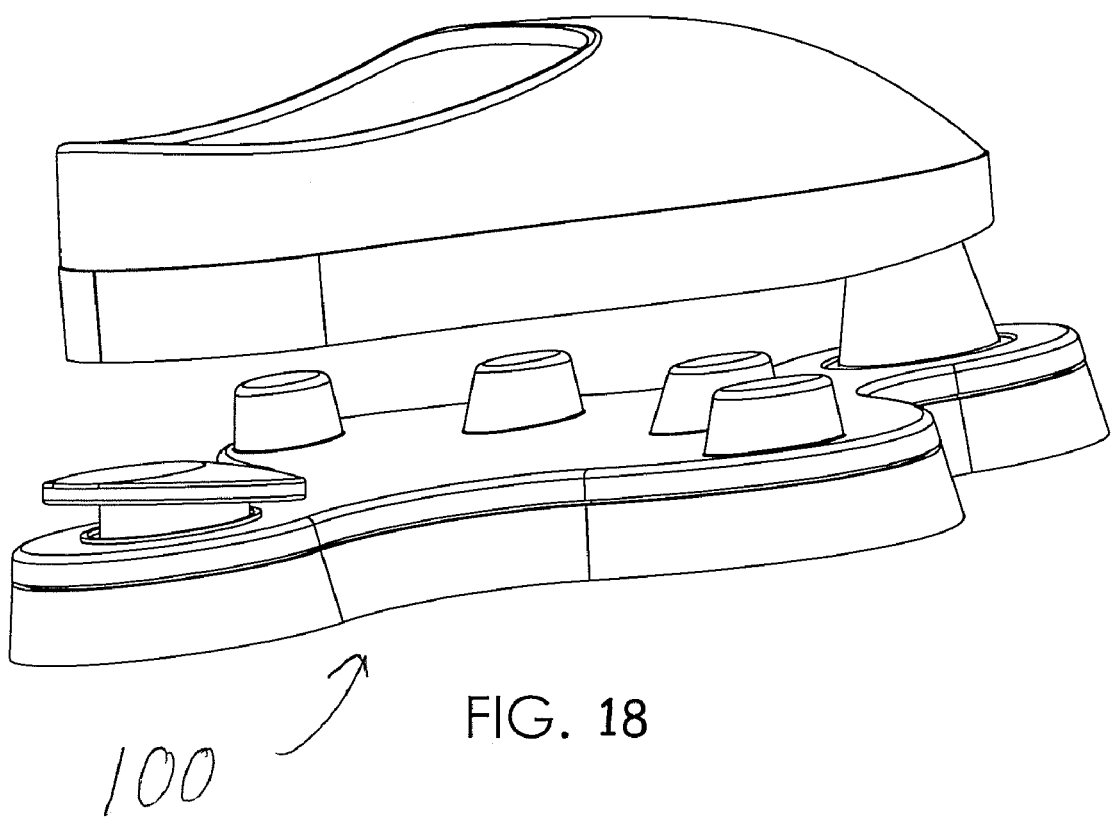
FIG. 18 is a right-side perspective view of the embodiment of FIGS. 13-17, illustrating the user operating the joystick/controller of the pad, wherein the user has lifted his/her heel up from the heal support.
Figure 19:
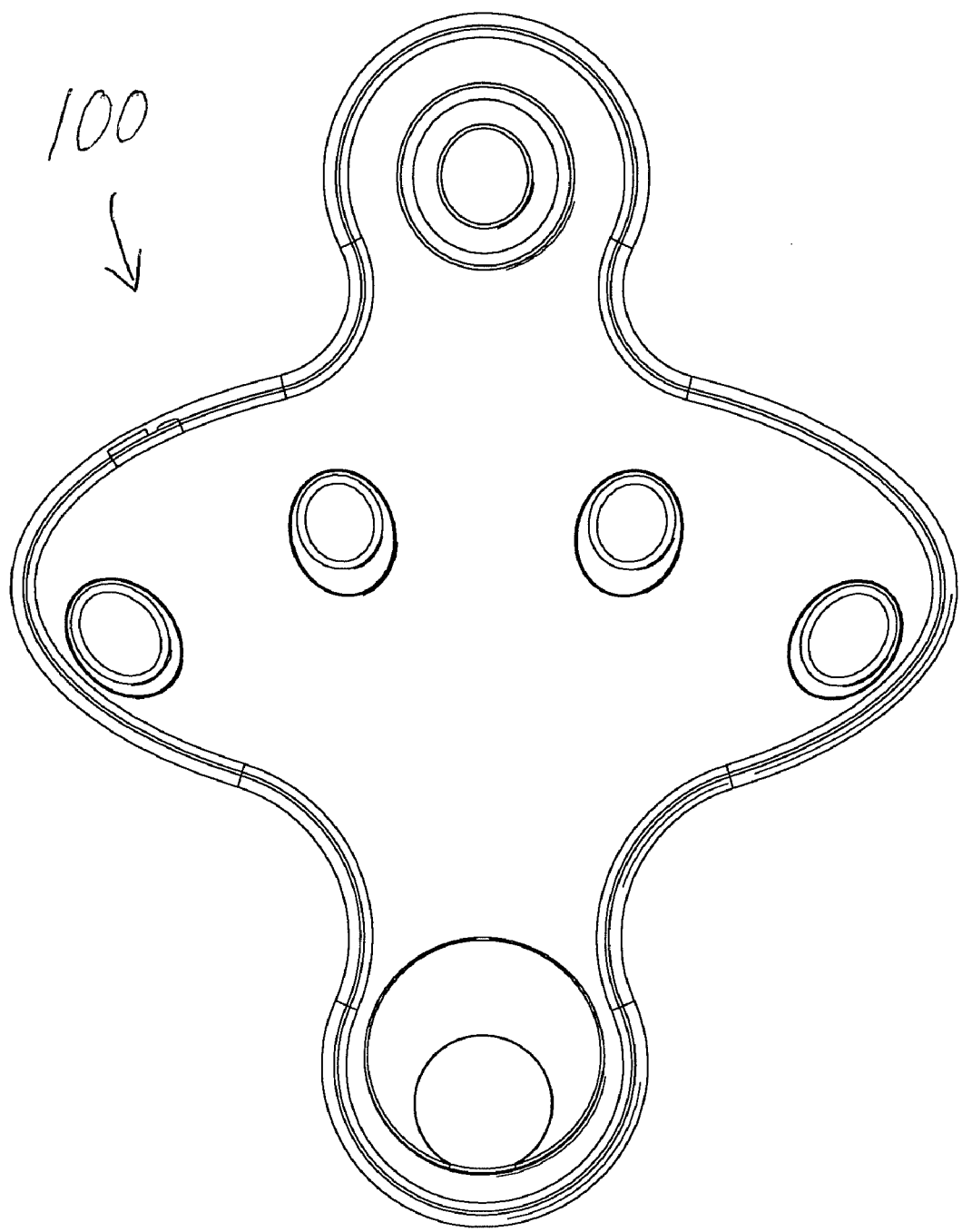
FIG. 19 is a top view of the embodiment of FIGS. 13-18.
Figure 20:
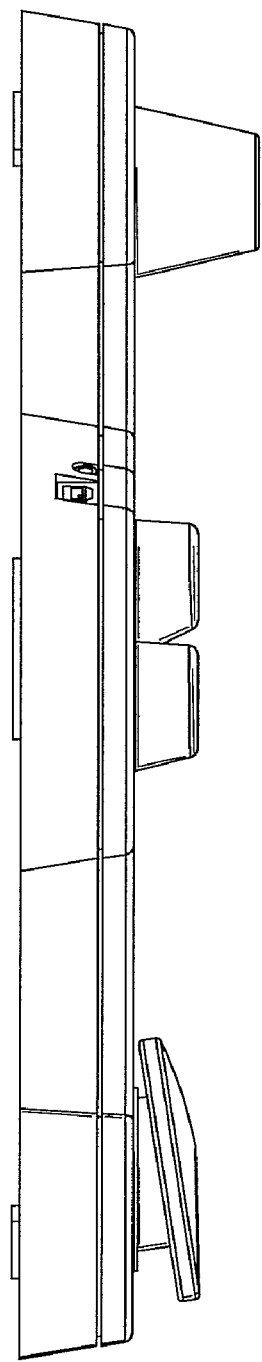
FIG. 20 is a left side view of the embodiment of FIGS. 13-19.
Figure 21:
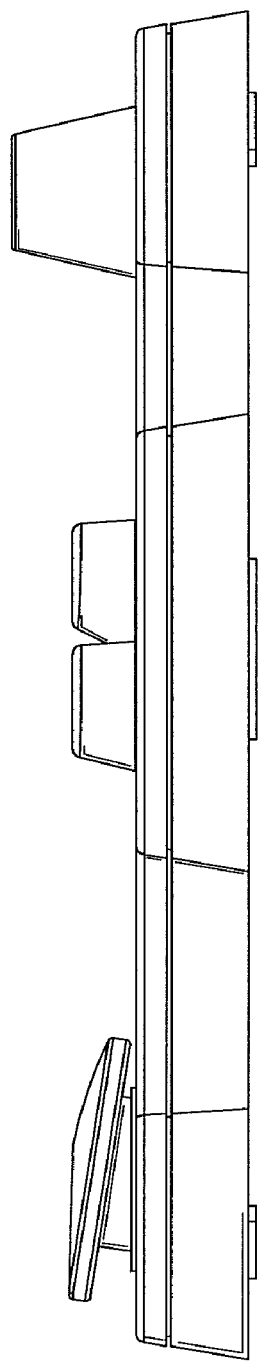
FIG. 21 is a right side view of the embodiment of FIGS. 13-20.
Figure 22:
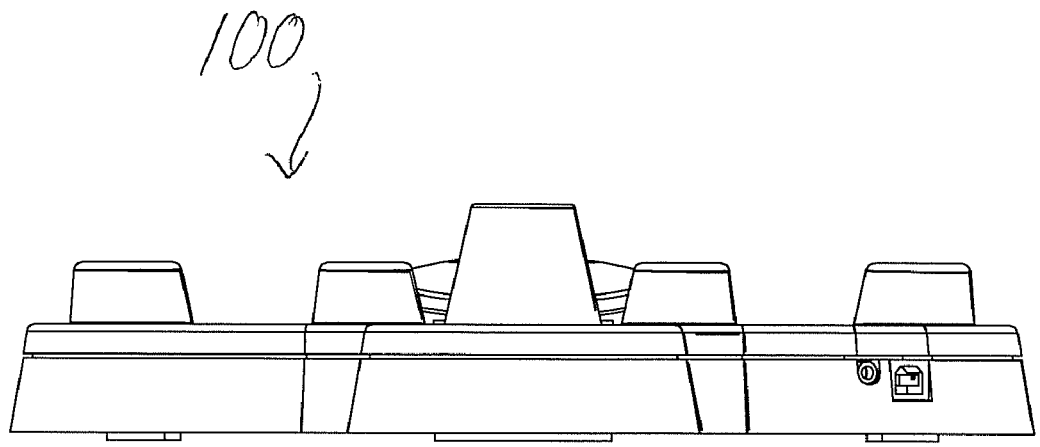
FIG. 22 is a front view of the embodiment of FIGS. 13-21.
Figure 23:
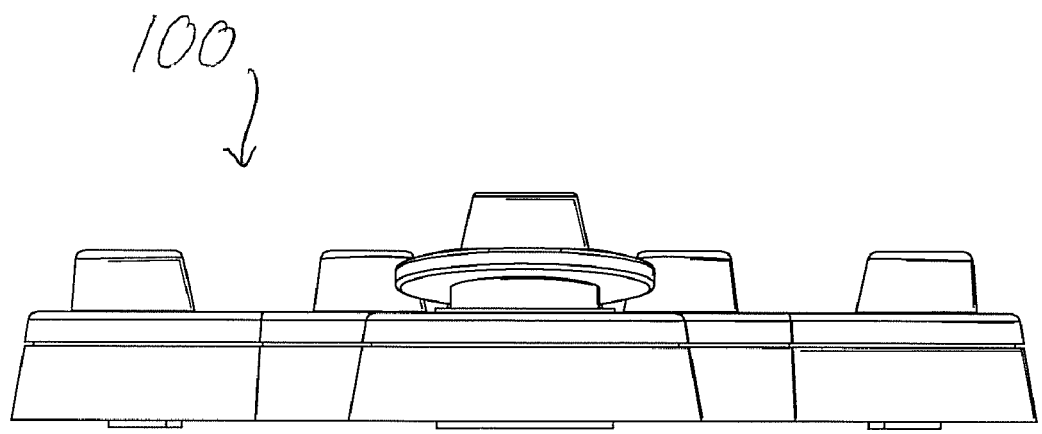
FIG. 23 is a rear view of the embodiment of FIGS. 13-22.
Figure 24:
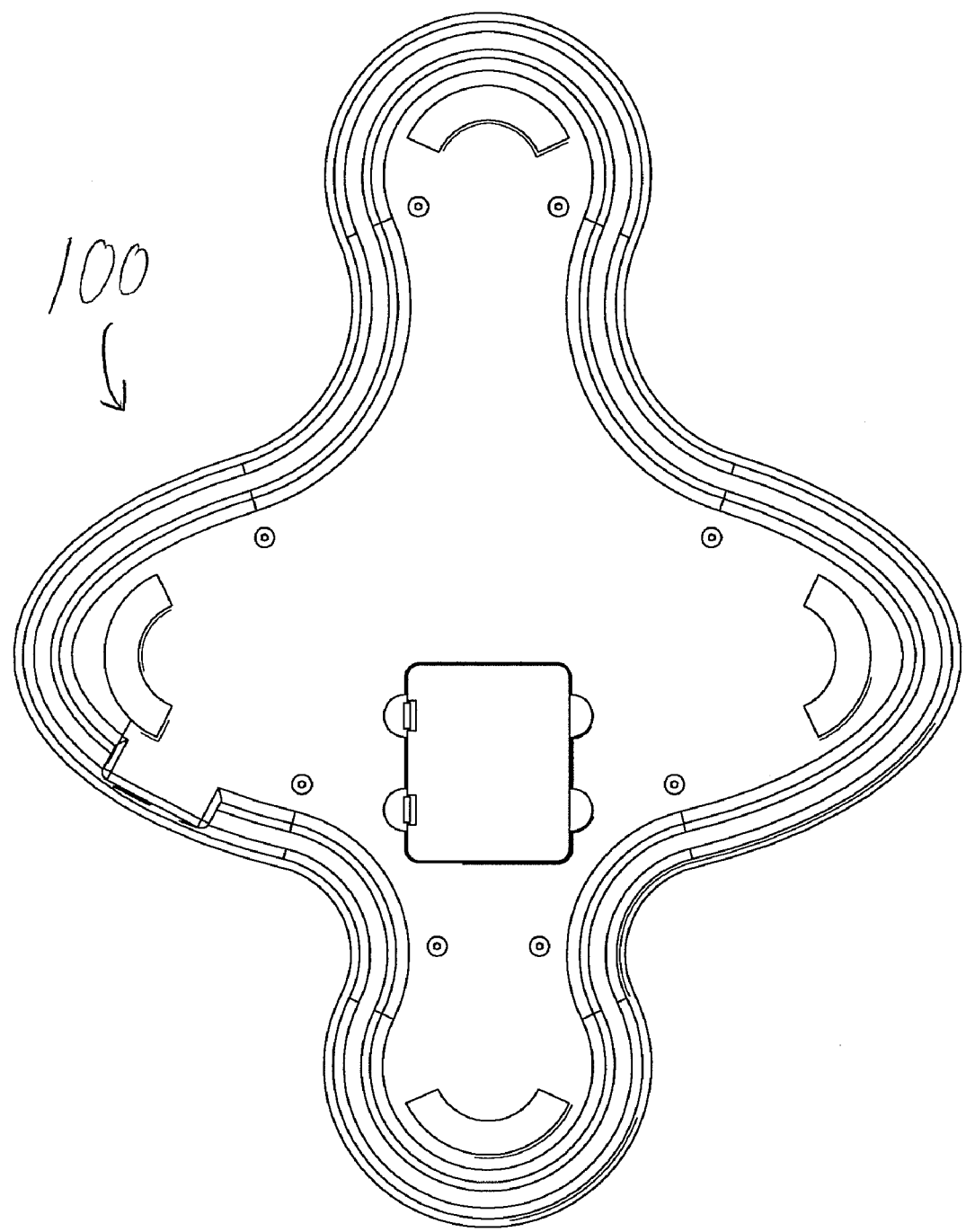
FIG. 24 is a bottom view of the embodiment of FIGS. 13-23.
Figure 25:
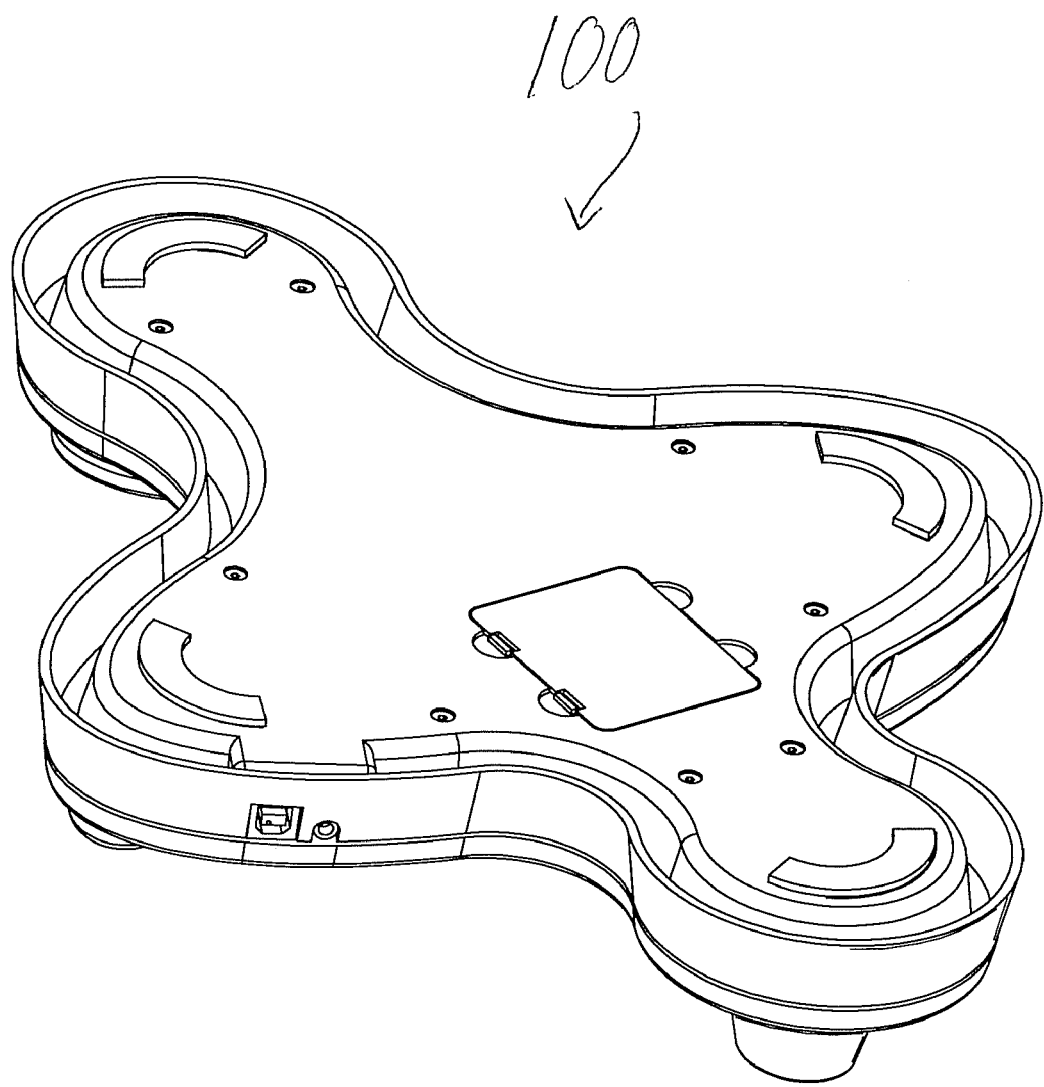
FIG. 25 is a perspective bottom view of the embodiment of FIGS. 13-24.
Figure 26:
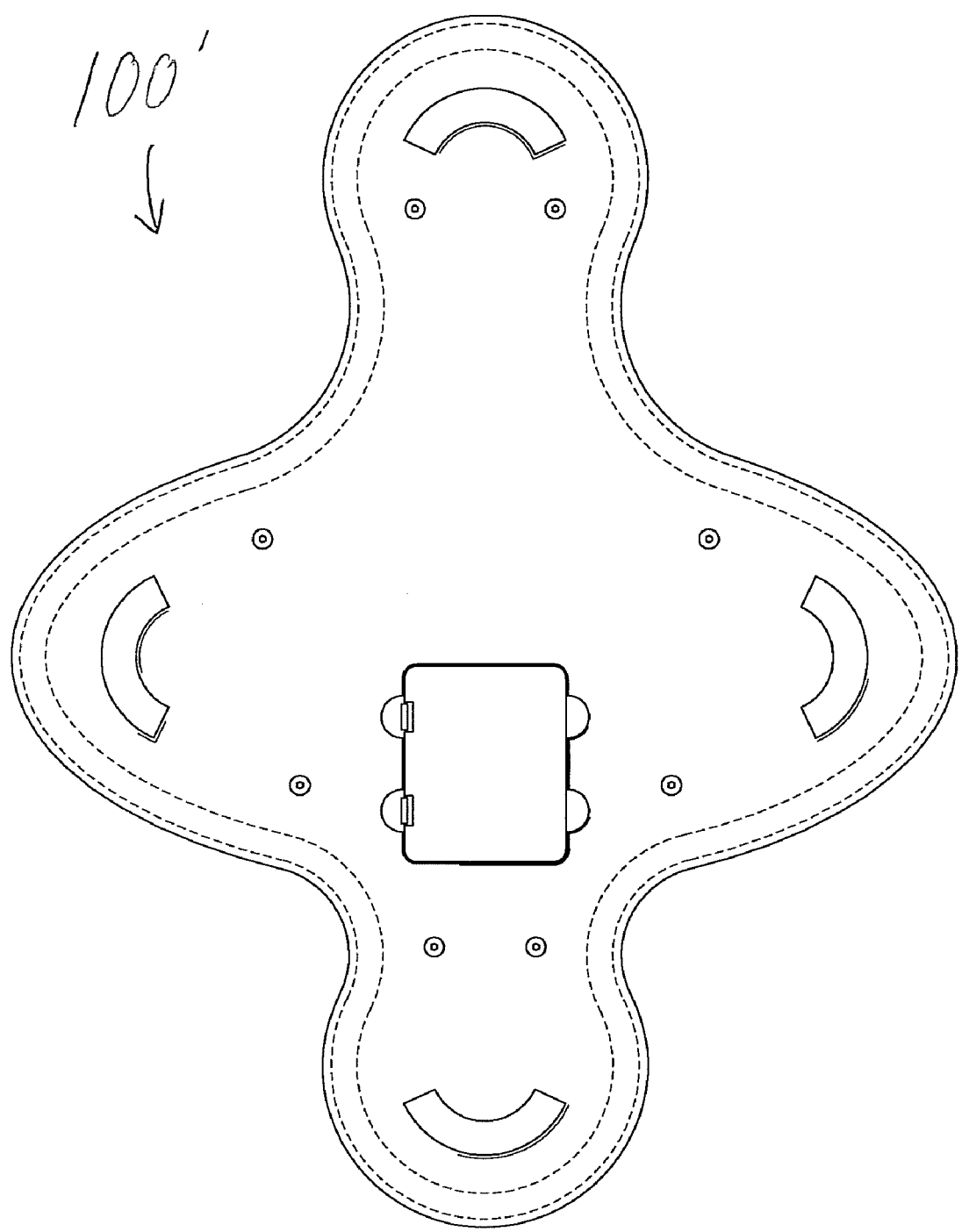
FIG. 26 is a bottom view of an alternative embodiment (100'), similar to that in FIGS. 13-23, but with broken lines emphasizing that alternative and/or simpler bottom surface features may be used.
Figure 27:
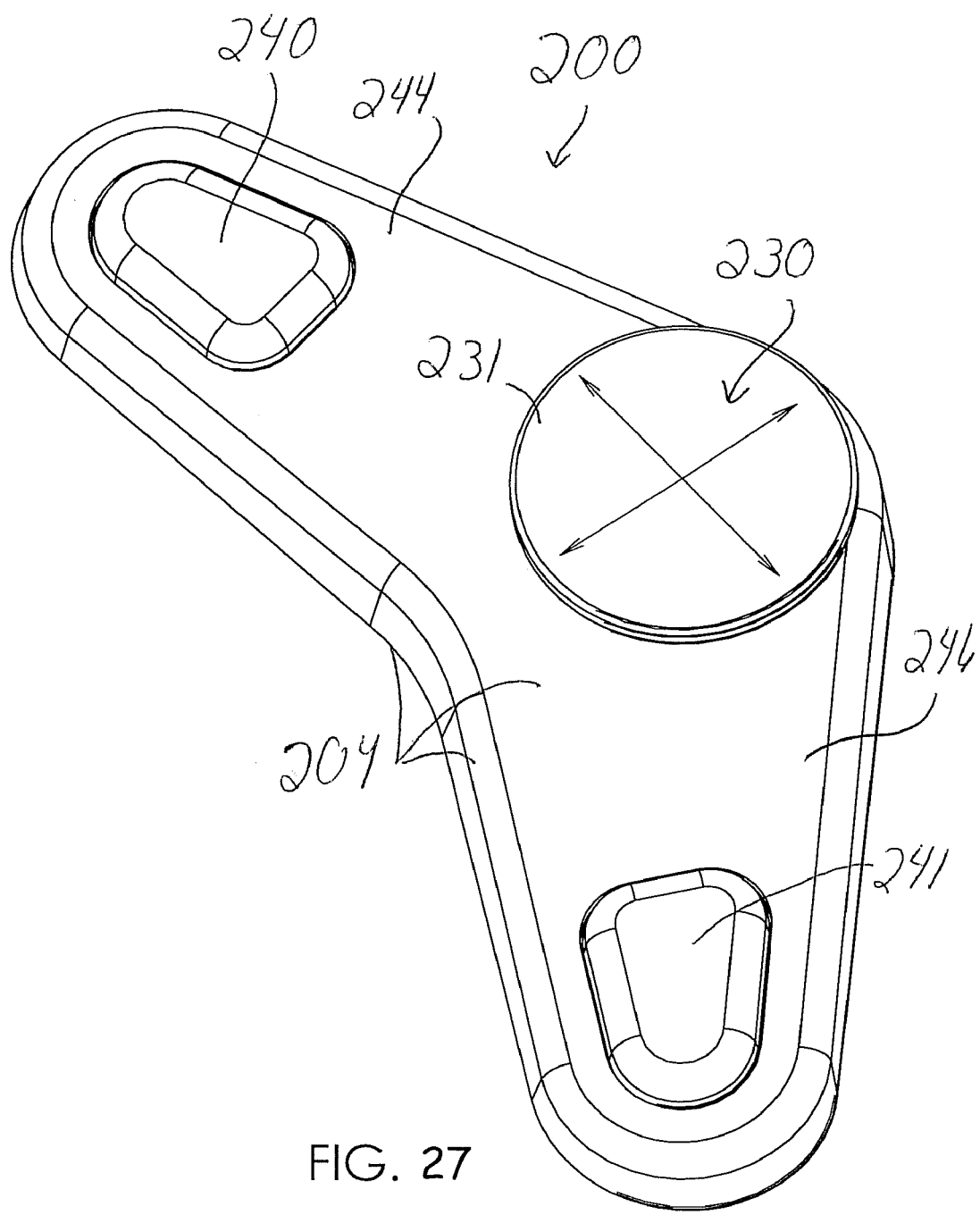
FIG. 27 is a top perspective view of an alternative embodiment having a central rocking cursor controller and right and left click buttons to the right and left sides of the cursor controller.
Figure 28:
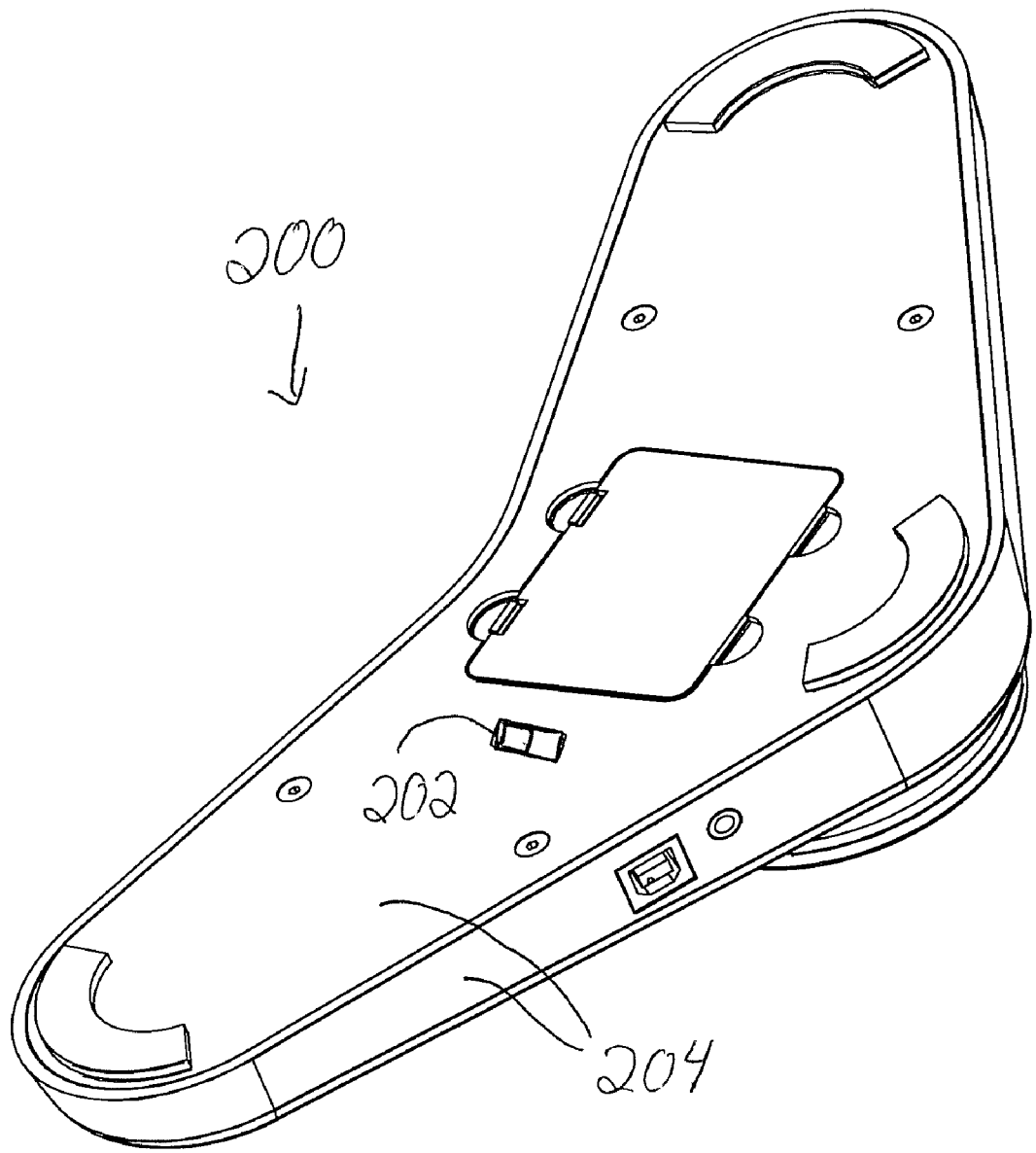
FIG. 28 is a bottom perspective view of the embodiment of FIG. 27.
Figure 29:
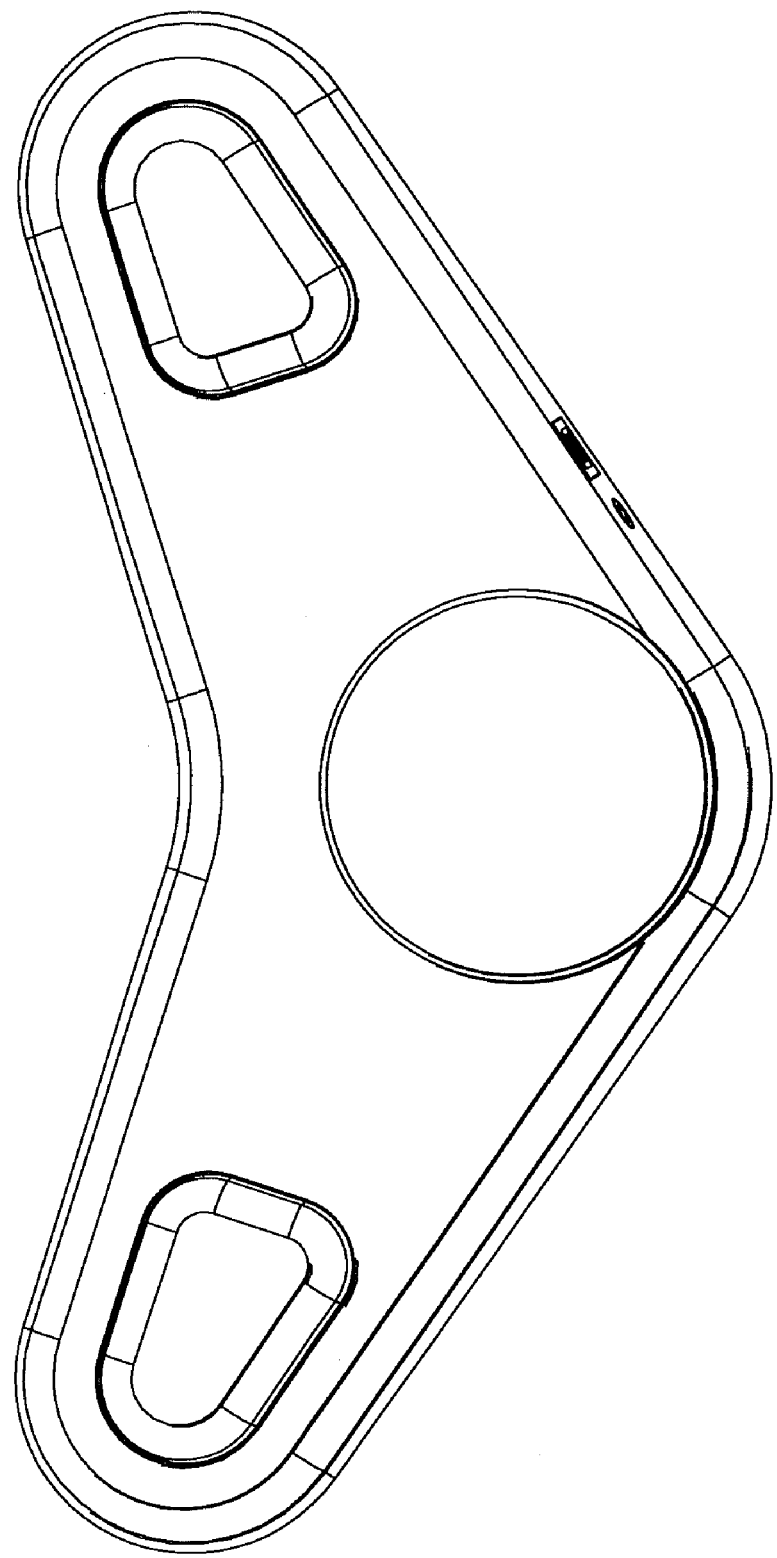
FIG. 29 is a top view of the embodiment of FIG. 27-28.
Figure 30:
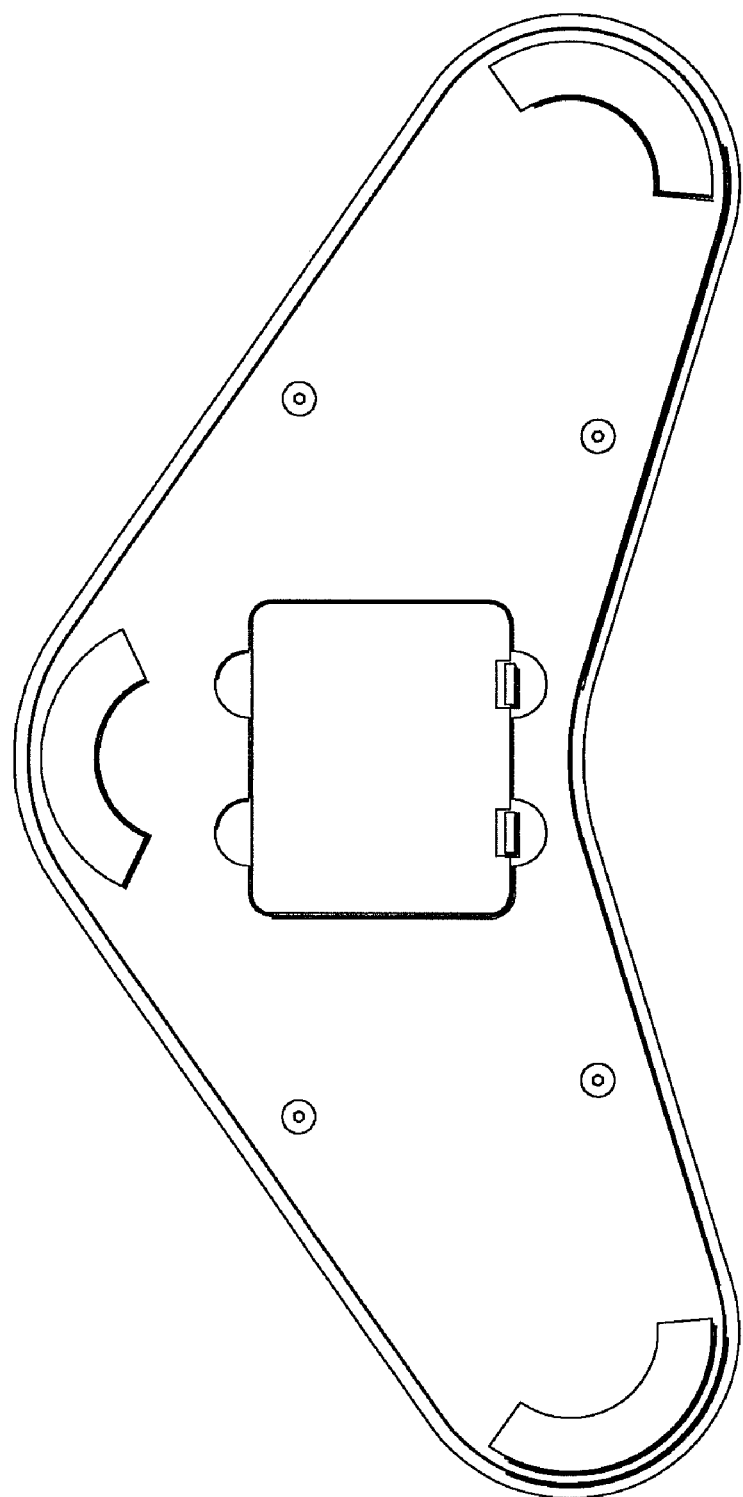
FIG. 30 is a bottom view of the embodiment of FIG. 27-29.
Figure 31:
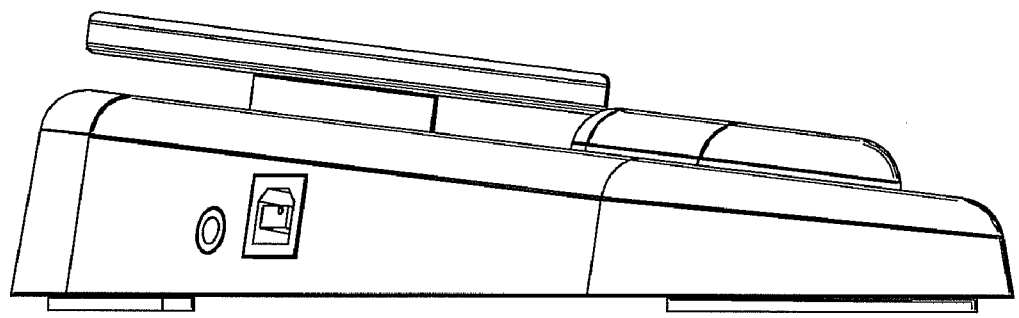
FIG. 31 is a left side view of the embodiment of FIG. 27-30.
Figure 32:
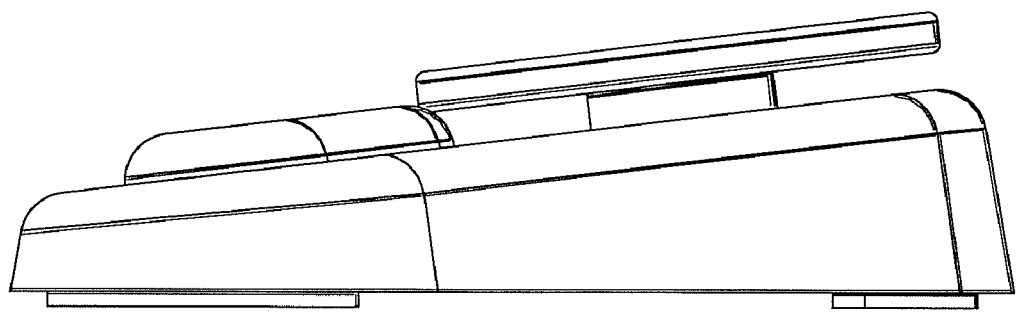
FIG. 32 is a right side view of the embodiment of FIG. 27-31.
Figure 33:
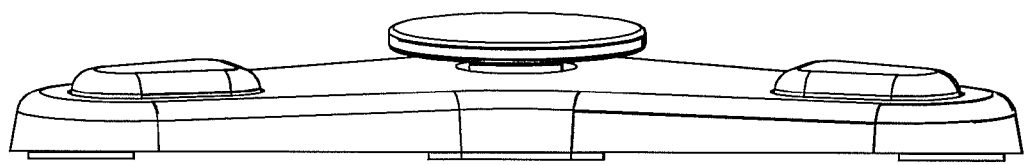
FIG. 33 is a rear view of the embodiment of FIG. 27-32.
Figure 34:
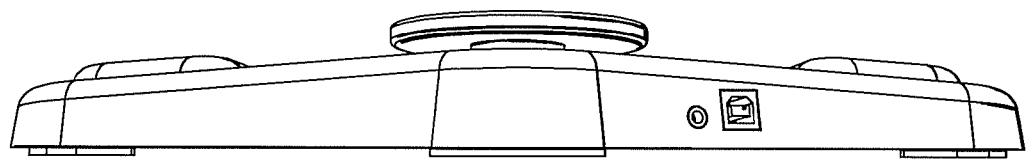
FIG. 34 is a front view of the embodiment of FIG. 27-33.
Figure 35:
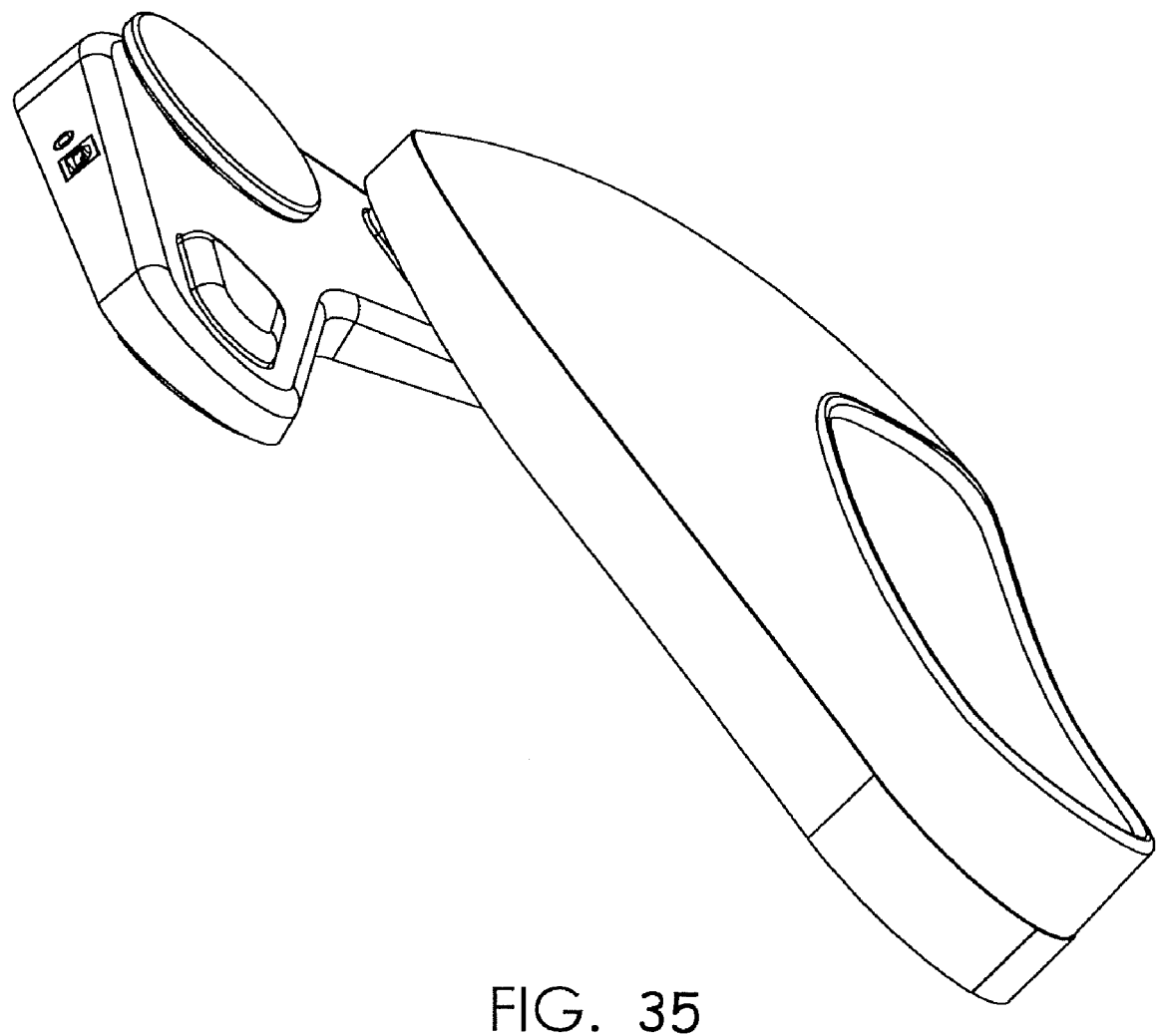
FIG. 35 is a left perspective view of the embodiment of FIGS. 27-34, with a shoe illustrating use of the pad.
Figure 36:
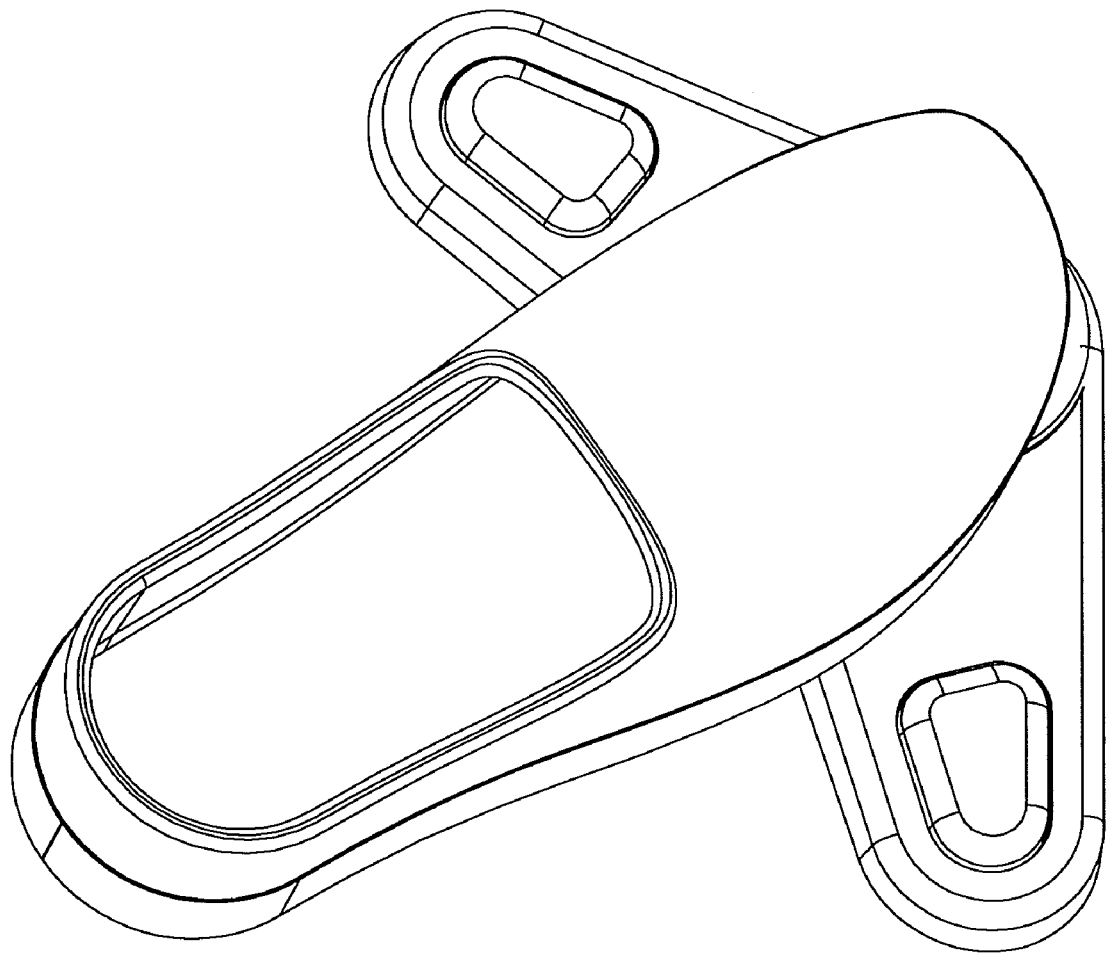
FIG. 36 is a top view of the embodiment of FIGS. 27-35, with the user operating the cursor controller.

An especially-preferred embodiment of the invented data entry pad is shown in FIG. 13. This data entry pad 100 comprises a main body 102 having a shape that may be described as generally cross-shaped, with a front arm 104, a rear arm 106, and right and left aims 108, 109. All of said "arms" are preferably integral portions of the main body 102, which preferably has a generally horizontal but slightly concave upper surface. Other pad shapes and surface contours may be used.

The heel support area 120 is on the rear arm 106, and preferably comprises a relatively large heel support 122 having the appearance of a flat, round button or heel rest without any upending walls or vertical guides for heel placement. The heel support 122 preferably has two functions: first, to serve as a rest location for receiving the heel, wherein the Support 122 is positioned, shaped, and raised so that it is easy for the user to place and retain his/her heel there; and, second, to serve as a rocking switch that has a "mouse click" function, most preferably a "left click" function. The heel support 122 is adapted in its structure and connection to the main body and the electronics so that force from the heel in a vertical downward direction allows no movement of the heel support 122, so that the heel support 122 acts only as a heel rest. However, when the user rocks his heel rearward while pressing on the heel support 122, the preferred heel support 122 also rocks rearward and affects a switching function, that is, makes a "left click." The heel support 122 is preferably designed so that it can take substantial force in the straight-downward direction without moving and without any switch function, but, upon purposeful rearward rocking of the heel support 122, the "click" or other switch is performed. Said purposeful rearward rocking of the heel preferably comprises pivoting of the heel support 122 by the heel to the full extent allowed by the main body and/or the pivotal connection of the heel support to the main body or other pad mechanical structure, but typically this extent will be a small amount such as 2-20 degrees and more preferably in the range of about 5-15 degrees from horizontal.

It may be noted that the preferred heel support 122 has a generally horizontal top surface when it is in the upright, rest position. In a case, as is preferred, wherein the main body of the pad 100 is generally horizontal and meant to rest on a flat floor, the foot will naturally rest on the pad so that the heel presses straight, vertically downward on the approximate center of the support 122 top surface. Therefore, the heel support is described herein as being immovable when downward vertical pressure is applied. Another way to describe the structure and function of the heel support 122 would be to say that the heel support is immovable when pressure is applied by the heel that is substantially perpendicular to the heel support top surface, and that the heel support tilts/pivots/rocks backwards when pressure is applied that is substantially non-perpendicular to its top surface.

After reading this disclosure, one of skill in the alt will be able to make such a heel rest that has a first (rest) position in which the heel rest is "upright" (not tilted or pivoted relative to the main body) and not moving in response to downward pressure, and that has a second (switch) position to which the heel rest rocks rearward (tilted or pivoted rearward relative to the main body) to send a electronic or electrical signal.

The controller 130 on the front arm 104 is a joystick-type controller to move a cursor/arrow on the cooperating computer screen, as generally discussed above for other embodiments. Controller is located in a position forward of the normal foot location, so that the foot may be moved forward on the pad 100 to operate the controller 130 with a distal end of the foot. Thus, this controller may be called a "toe" controller.

Four foot buttons 140 are provided in a generally radial planar pattern, for example, in a curved arc near the middle of the pad 100 with the center of the arc preferably being on or near the heel support 122.

As with the other embodiments discussed herein, different numbers or arrangements of foot buttons may be provided, preferably with all of these being easily reachable with minor foot movement. Especially-preferred are buttons that are arranged in an arc wherein the heel may rest on the heel support 122 while the foot is being pivoted in a generally horizontal plane to reach the various foot buttons. As discussed above for other embodiments, the foot buttons 140 are preferably fairly close together, each in their own small circle sector. The "one," "two," "three," and "four" buttons correspond to the numbers 1 and 5, 2 and 6, 3 and 7, and 4 and 8, as previously explained for the preferred embodiment. Preferably, further pressing of the "four" button (after the data value 8, for example, for three or more seconds, or for more than three seconds, or for another time typically greater time mark) may serve as a "right click" switch. Preferably, other buttons or controllers are forward of the arc of foot buttons, so that the foot might need to be moved forward but preferably not rearward; it is preferable that the foot not move off of the pad 100 either in the sideways or rearwards directions. Also, as will be understood by the disclosure herein, the pad 100 may be adapted so that the buttons operate according to a code of actuation that depends upon the number of times of pressing and releasing and then pressing again, rather than the continuous duration of pressing the button.

The preferred embodiments are designed for entering periodontal data—e.g., the depth of gingival sulcus. Based on the needs of this application, the preferred embodiment has four foot buttons and is capable of entering data values from one to eight, inclusive. For example, the user would take a measurement with an instrument—e.g., a 3. The third foot button of the data entry pad is then pressed and promptly released to enter this value. If necessary, the controller is used to move a cursor, or similar pointer, to another data entry field on the screen. The next measurement is taken and recorded—e.g., a 5. The first foot button of the data entry pad is pressed and held until the data value is incremented to 5. It is then released and the data value is recorded. This process continues until all necessary measurements are taken and recorded. In cases wherein the measurements are always taken in the same order, and the software is adapted to receive this order of measurements, there may be no need for controller use between the measurements.

Although the preferred embodiments have been described as applied to recording the depths of gingival sulcus, it may be used to enter data for any purpose without exceeding the scope of the invention. Also, especially-preferred embodiments may be for simpler applications, such as foot-operated input into a computer and/or other equipment that comprises mainly or solely cursor control and instruction input such as a single piece of information per button or binary information per button. For example, one pad 200 that only has a cursor controller and two buttons is shown in FIGS. 27-36. This pad 200 may be described as a "boomerang" shape, with a plurality of foot buttons 240, 241 and preferably a cursor controller 230 being in an arc-pattern or angled pattern on the pad 200. The foot buttons 240, 241 and cursor controller 230 preferably have top surfaces that are generally but not necessarily exactly, on the same plane and so are arranged in what may be called a "radial planar pattern."

The cursor controller 230 is preferably a rocking plate 231 that may be rocked/pushed in any direction, allowing "pointing" in any direction 360 degrees around its outer perimeter. This rocking cursor controller may be made according to known technology for making a cursor controller of this type, wherein multiple switches are provided underneath the plate 231 for actuation by the rocking plate to sense and send signals indicating the direction of the pointing, and, hence, the direction of desired cursor travel. Alternatively, but less preferably, a ball-style cursor controller, also known in the computer arts, may be used instead of the rocking plate.

The foot buttons 240, 241 are provided on left and right wings 244, 246 of the pad 200, in positions rearward from the controller 230 so that the front portion of the foot, when the foot is pivoted to the left or right, can conveniently press on the buttons 240, 241. Each button 240, 241 is preferably near the outer end of its respective wing 244, 246, with the center of each button 240, 241 being approximately 1 foot-width away from the center of the controller 230. This way, the foot, when pressing downward on either of the buttons 240, 241, will not interfere with or operate the controller 230.

The two wings 244, 246 are each preferably elongated and straight or substantially straight, and joint at the centerline of the pad 200 (on the center of the control 230 plate) at an angle of 120-150 degrees, and, more preferably, at 135 degrees. Thus, because of this angled shape, one may call the pad 200 generally a "boomerang" shape.

The foot buttons 240, 241 are preferably adapted by the electronics of the pad and/or cooperating computer to be "left click" and "right click" buttons, for performing the tasks normally associated with the conventional mouse buttons of the same name. However, the pad 200 and/or the cooperating computer may be adapted to give buttons 240, 241 other tasks such as data entry (for example, numbers selected from a range of numbers) or additional tasks based on longer duration of pressing the button and/or on time of sequential pressing, as explained in detail above for the preferred dentistry embodiments.

The left wing 244 and the left button 240 will typically be the "left click" portion and button for the user, and the right wing 246 and the right button 241 will typically be the "right click" portion and button for the user. However, the pad 200 preferably is adapted to switch the purposes of the buttons, for example, for a person who is strongly left-handed/footed, and/or is not able to use his/her right foot, and wants button 241 to be the "left-click" button and button 240 to be the "right-click" button, that is, mirror-image use and operation. This configuration would typically be used by a person who uses their left foot for operation of the pad 200. The housing and the button and controller arrangement is preferably symmetrical and the two wings are mirror images, so that the pad may be switched between right and left foot use without any confusion or discomfort. A switch 202 may be provided on a surface of the pad housing 204, so that it is easily accessible to a user to switch between the two "mirror-image" operation modes.

Pad 200 preferably does not have a heel rest portion or extension. The heel will normally rest on the floor and the user will pivot the foot to reach the two buttons 240, 241 and the controller 230. Alternatively, but less preferably, the user will lift his/her heel up off the floor while manipulating the cursor controller 230 with the front portion of the foot.

Although the preferred embodiments have been described as including one data entry pad, a second pad could be added. The user could use both feet and the number of foot buttons that could be included would be expanded. Also, as made clear by the embodiment of FIGS. 27-36, the invented foot operated data entry pad may be adapted to input other than numerical data. For example, by adding or adapting foot buttons and/or using two data entry pads, the invention could be used to enter other types of data, such as alphanumeric symbols, words, or phrases. For example, buttons may correspond to pre-determined woods or phrases that are important and repeatedly used in a particular technology or health field; such word or phrase data entry using embodiments of the invention would eliminate the need to "type out" or point and click, by hand with a keyboard and mouse, on each of the words or phrases each time they need to be entered. Although the preferred embodiment has been described as having four foot buttons, it is not limited to any particular number of foot buttons and may be adapted to enter any numerical range just as a standard number pad on a keyboard—i.e., some embodiments of the data entry pad may enter digits 0 through 9, with a decimal point as needed, to input data values. Also, as make clear by the embodiment of FIGS. 27-36, the foot buttons may be used to input instructions and single pieces of information, rather than data comprising many numbers.

The preferred embodiments may include an automated voice system that announces data values at various points in the system's operation. Any conventional automated voice system may be used, and the voice may be broadcast from a built-in speaker(s) or over the computer system's audio system—e.g., by adding a connection to the computer's microphone jack. Alternatively, a simpler system, such as an audible beep, may be used to indicate that, for example, a data value has changed. However, this is less preferred because it increases the probability that the user will accidentally, and possibly unknowingly, enter an incorrect data value.

Many embodiments of the invention, therefore, may be described as a data entry and/or instruction input pad for a computer system comprising a foot button, said foot button being configured to enter different data values according to a code of actuation of the foot button or said foot button being configured to enter a single piece of data, binary data, and/or instructions. A code of actuation may depend upon how long the button is continuously depressed, or upon how many times the button is depressed, released, and re-depressed, for example. A plurality of foot buttons are preferably spaced-apart in a generally radial planar pattern on said pad, each of said foot buttons being distanced, in embodiments with a heel support portion or extension, about 5-10 inches from the center of a heel support portion or extension also on said pad.

A cursor controller may be provided, preferably farther from the heel support area than said foot buttons. Optionally, a mouse control button, for example, a light click or left click button, may be provided farther from the heel support area than said foot buttons, or, as illustrated by the embodiment in FIGS. 27-36 wherein the right and left click buttons are a main feature of the pad, the right and left click buttons may be part of the main "arc" of buttons. Alternatively, a mouse control button, a right click or left click button, may be provided in the heel support area. Alternatively, a mouse button function may be provided as one of the functions of one or more of the foot buttons.

Also, some embodiments may be described as being a foot key pad for a computer, which comprises a cursor controller and a mouse controller button, the cursor controller and mouse controller button being spaced-apart in a generally radial planar pattern on said pad, and both said cursor controller and said mouse controller button being distanced about 5-10 inches from the center of a heel support area also on said pad. The foot key pad may comprise a plurality of mouse controller buttons, and one mouse controller button may be in the heel support area, for example.

Computer systems using the preferred foot key pads may be described as a computer, finger keyboard, mouse, foot-operated key pad and a multiplexer to provide cooperation between said foot-operated key pad and the computer, wherein the foot-operated key pad comprises a heel support area and multiple foot buttons operated by the foot pressing on each button, the foot buttons preferably being arranged in an arc on a radius from a center (the center preferably being the heel support area). A computer system may comprise a computer, finger keyboard, mouse, foot-operated key pad and a multiplexer, wherein: the finger keyboard, mouse and foot-operated keypad are connected to the inputs of the multiplexer; the output of the multiplexer is connected to the computer's input; and the multiplexer is configured to feed information to the computer in the order it is input by the user of the system from the finger keyboard, mouse, and foot-operated key pad.

Embodiments of the invention may include a method of data entry with a foot-operated key pad comprising a foot button, the method comprising a code of actuation of said button with a timing feature. A method of data entry, with a foot operated key pad comprising a foot button, may comprise a code of actuation of said foot button with a repeat feature wherein the code of actuation depends upon how many time the foot button is sequentially pressed (without any other buttons being pressed or controllers on the key pad being operated in between said pressings of said foot button).

Although this invention has been described above with reference to particular means, materials, and embodiments, it is to be understood that the invention is not limited to these disclosed particulars, but extends instead to all equivalents within the scope of following Claims.

I claim:

1. An input pad for a computer comprising a pad housing, and a plurality of foot buttons and a cursor controller arranged on a top surface of the pad housing in an arc, wherein a first button of said foot buttons is on a left side of the cursor controller and a second button of said foot buttons is on a right side of the cursor controller, wherein each of said first button and said second button is adapted to be both a right-click button and a left-click button for cooperating with said computer when switched between right-click operation and left-click operation by a switch accessible from an outside surface of the pad housing.

2. An input pad as in claim 1, wherein said pad housing has a right wing and a left wing, said right wing and left wing being substantially straight and elongated and joining at an angle of 120-150 degrees to each other.

3. An input pad as in claim 1, wherein the pad housing consists only of a right wing and a left wing, said right wing and left wing being substantially straight and elongated and joining at an angle of 120-150 degrees to each other.

4. An input pad as in claim 1, wherein said cursor controller comprises a generally flat-topped rocking plate.

5. The input pad of claim 1, wherein said plurality of foot buttons are spaced-apart in a generally radial planar pattern on said pad, each of said foot buttons being distanced about 5-10 inches from a center of said rocking heel rest.

6. An input pad for a computer comprising a pad housing having four arms extending out from a center of the pad housing in a cross-shape, a plurality of foot buttons arranged on a top surface of the pad housing in an arc transversely extending across the pad housing so that some of said foot buttons are near the said center of the pad housing and some of said foot buttons are located on two of said arms that are a right and a left arm;

the input pad further comprising a cursor controller located on a third of said arms that is a forward arm; and a rocking heel rest located on a fourth of said aims that is a rearward arm, wherein said hell rest is adapted to remain unmoving upon downward pressure and to rock rearward upon rearward pressure, and, wherein, when said heel rest rocks rearward, it performs a mouse click function.

7. An input pad as in claim 6, wherein the pad housing has a length extending between said forward arm and said rearward arm, and said plurality of foot buttons consist of four buttons spaced apart transversely across the pad housing perpendicular to said length.

8. An input pad as in claim 6, wherein multiple of said plurality of foot buttons are configured to enter different data values according to a code of actuation of the foot button, wherein said code of actuation comprises a first data value being transmitted to the computer when the foot button is continuously pressed for less than one second and released, and a second data value being transmitted to the computer when the foot button is continuously pressed for one second or more and then released.

9. The input pad of claim 8, wherein said code of actuation further comprises a third signal being sent to said computer when the foot button is continuously pressed for three seconds or more.

10. The input pad of claim 8, wherein said code of actuation further comprises a third signal being sent to said computer when the foot button is continuously pressed for more than three seconds.

11. The input pad of claim 6, wherein, when said heel rest rocks rearward, it performs a left-click function.

* * * * *